US009951093B2

(12) United States Patent
Lindhorst et al.

(10) Patent No.: US 9,951,093 B2
(45) Date of Patent: Apr. 24, 2018

(54) CHIRAL COMPOUNDS SUBSTITUTED WITH PHOSPHONIC ACID ESTER FUNCTIONS OR PHOSPHONIC ACID FUNCTIONS

(75) Inventors: Thomas Lindhorst, Innsbruck (AT); Birgit Werner, Innsbruck (AT); Holger Bock, Innsbruck (AT)

(73) Assignee: UGISense AG, Munich (DE)

( * ) Notice: Subject to any disclaimer, the term of this patent is extended or adjusted under 35 U.S.C. 154(b) by 193 days.

(21) Appl. No.: 13/527,217

(22) Filed: Jun. 19, 2012

(65) Prior Publication Data

US 2013/0131019 A1    May 23, 2013

Related U.S. Application Data

(63) Continuation of application No. 12/374,440, filed as application No. PCT/EP2007/006483 on Jul. 20, 2007, now abandoned.

(30) Foreign Application Priority Data

Jul. 21, 2006 (DE) ........................ 10 2006 034 319

(51) Int. Cl.
*C07F 9/6512* (2006.01)
*C07K 14/00* (2006.01)
*A61K 38/00* (2006.01)

(52) U.S. Cl.
CPC ........ C07F 9/65121 (2013.01); C07K 14/003 (2013.01); *A61K 38/00* (2013.01)

(58) Field of Classification Search
None
See application file for complete search history.

(56) References Cited

U.S. PATENT DOCUMENTS

| 5,719,262 | A | 2/1998 | Buchardt et al. |
| 7,105,648 | B1 | 9/2006 | Bock et al. |

FOREIGN PATENT DOCUMENTS

| WO | WO 95/16202 | 6/1995 |
| WO | WO 98/03542 | 1/1998 |
| WO | WO 00/52038 | 9/2000 |

OTHER PUBLICATIONS

Isidro-Llobet et al Chem Rev (109:2455-2504, 2009).*
Will et al. (Tetrahedron 51(44):12069-12082, 1995).
STN Search Report Accession No. 1995:908968.
Hyrup, Birgitte et al.: "Peptide Nucleic Acids (PNA): Synthesis, Properties and Potential Applications", *Bioorganic & Medicinal Chemistry*, vol. 4, No. 1, 1996, pp. 5-23.
Schick, Andreas et al.: "Synthesis of Phosphonate Analogues of Sphinganine-1-phosphate and Sphingosine-1-phosphate", *Tetrahedron*, vol. 51, No. 41, 1995, pp. 11207-11218.
Kofoed, Thomas et al.: "PNA Synthesis Using a Novel Boc/Acyl Protecting Group Strategy", *Journal of Peptide Science*, 7, 2001, pp. 402-412.
Thomson, Stephen A. et al.: "Fmoc Mediated Synthesis of Peptide Nucleic Acids", *Tetrahedron*, vol. 51, No. 22, 1995, pp. 6179-6194.
Breipohl, Gerhard et al.: "Novel Synthetic Routes to PNA Monomers and PNA-DNA Linker Molecules", *Tetrahedron*, vol. 53, No. 43, 1997, pp. 14671-14686.
Christensen, Leif et al.: "Solid-phase Synthesis of Peptide Nucleic Acids", *Journal of Peptide Science*, vol. 3, 1995, pp. 175-183.
Koch, Troels et al.: "Improvements in automated PNA synthesis using Boc/Z monomers", *J. Peptide Res*, 49, 1997, pp. 80-88.
Schollkopf, Ulrich et al.: "Asymmetric Synthesis of Various Non-Proteinogenic Amino Acid Methyl Esters (Functionalized in the Carbon Chain) and Amino Acids by the Bishctim Ether Method", *Liebigs Ann. Chem.*, 1986, pp. 2150-2163.
Piccart-Gebhart, M.D., Martine J. et al.: "Trastuzumab after Adjuvant Chemotherapy in HER2-Positive Breast Cancer", *The New England Journal of Medicine*, Oct. 20, 2005, vol. 353, No. 16, pp. 1659-1672.
Haaima, Gerald et al.: "Peptide Nucleic Acids (PNAs) Containing Thymine Monomers Derived from Chiral Amino Acids: Hybridization and Solubility Properties of D-Lysine PNA", *Angew Chem. Inv. Ed. Eng.*, 1996, vol. 35, No. 17, pp. 1939-1942.
Bergmann, Frank et al.: "Solid Phase Synthesis of Directly Linked PNA-DNA-Hybrids", *Tetrahedron Letters*, vol. 36, No. 38, 1995, pp. 6823-6826.

* cited by examiner

*Primary Examiner* — Craig D Ricci
(74) *Attorney, Agent, or Firm* — Hang Partners LLP

(57) ABSTRACT

The present invention relates to novel compounds that contain PNA units substituted with phosphonic acid ester functions or phosphonic acid functions, and have at least one chiral center. The compounds may be used for the treatment of viral diseases, such as AIDS.

14 Claims, 5 Drawing Sheets

Non-infected M8166　　　　HIV-infected M8166

Figure 5

Localisation of the compounds according to the invention in the gastrointestinal tract and the air bladder of Medaka fishes (day 1 after the transfer into fresh water)

gastrointestinal tract and air bladder of the Medaka fish

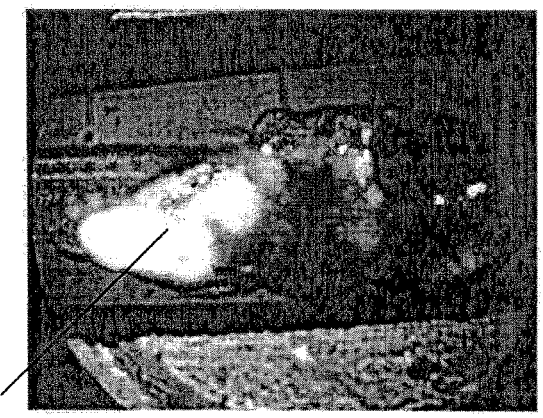

Localisation of the compounds according to the invention in the gastrointestinal tract and the air bladder of Medaka fishes (day 2 after the transfer into fresh water)

gastrointestinal tract and air bladder of the Medaka fish

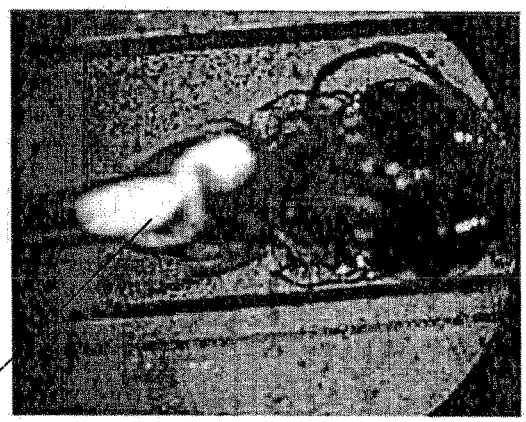

Localisation of the compounds according to the invention in the gastrointestinal tract and the air bladder of Medaka fishes (day 5 after the transfer into fresh water)

gastrointestinal tract and air bladder of the Medaka fish

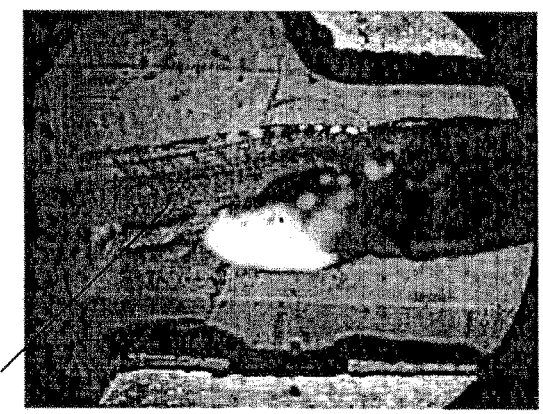

CHIRAL COMPOUNDS SUBSTITUTED WITH PHOSPHONIC ACID ESTER FUNCTIONS OR PHOSPHONIC ACID FUNCTIONS

This application is a continuation of U.S. patent application Ser. No. 12/374,440 filed Jul. 9, 2009 which is a 371 application of PCT/EP2007/006483 filed Jul. 20, 2007 which claims priority benefits to German Patent Application Number 10 2006 034 319.0 filed Jul. 21, 2006, the disclosures of all are herein incorporated by reference.

The present invention relates to novel compounds which contain PNA units substituted with phosphonic acid ester functions or phosphonic acid functions, and which exhibit at least one chiral center.

After the primary infection of a host cell by a HI virus, the known antiviral compounds (for example Indinavir) exhibit an action only upon the immediate first viral daughter generation by interrupting the replication cycle. This circumstance results in a measurable reduction of the number of the viruses compared to untreated host cells. This reduction of the number of the viruses, however, does not happen to 100%. If surviving viruses are isolated, they are further on capable of infecting host cells which have been not infected before, and passing through a complete replication cycle.

PNAs (peptide nucleic acids) are synthetic DNA/RNA analoga having a N-(2-amino-ethyl)glycine frame (NB=nucleobase, n=0-50; $R^1$, K, L=substituents). PNAs are produced by connecting peptide bonds between N-acetyl N-(2-aminoethyl)glycine building blocks (PNA monomers). Each of these individual N-acetyl N-(2-aminoethyl)glycine building blocks represents a PNA unit.

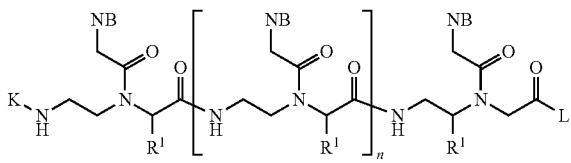

PNAs are resistant to a hydrolytic (enzymatic) cleavage under physiological conditions. It is known that PNAs may recognize complementary nucleic acid sequences (DNA or RNA) in a sequence specific manner and can bind to those with a higher affinity than their natural prototypes (M. Egholm, O. Buchardt, L. Christensen, C. Behrens, S. M. Freier, D. A. Driver, R. H. Berg, S. K. Kim, B. Norden, P. E. Nielsen, Nature, 1993, 365, 566-568. B. Hyrup, P. E. Nielsen, Bioorg. Med. Chem., 1996, 4, 5-23).

PNAs are applied for example as antisense oligomers. In this context, the expression of the proteins is inhibited by hybridization of an antisense oligomer to the protein specific mRNA on the level of translation. As a result of these properties, PNAs are suitable compounds, for example, for the use as diagnostics.

Known PNA molecules show the disadvantage that they are hardly water soluble, compared with DNA. Furthermore, the permeation of the cell membrane is a general problem for PNAs so that the reception into the cells occurs extremely slowly only.

From U.S. Pat. No. 5,719,262 PNAs are known whose water solubility could be enhanced by amine functions at the rest $R^1$. However, also PNAs modified in such a way exhibit still a poor cell permeability. Thus, the use of PNAs as antisense active agents in living organisms is very limited.

From EP 1157031 oligomers are known which exhibit one or more phosphonic acid ester functions or phosphonic acid functions. Oligomers modified in such a manner have a better cell permeability compared with PNAs which do not contain these substituents.

Admittedly, a good cell permeability of antisense oligomers exclusively is not sufficient in order to achieve a strong effect of repression of the gene expression in biological systems.

Therefore, it is the object of the present invention to provide compounds that not only are able to reduce the number of viruses of the first daughter generation, but also additionally demonstrate an intensified reducing effect on the number of the viruses of the second daughter generation, as well as applications thereof. Thus, one receives a class of substances capable of demonstrating an effectiveness over two generations of viruses.

This object is solved by compounds of the general formula I:

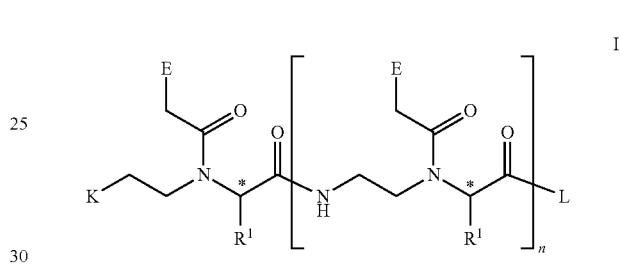

wherein n represents an integer from 7 to 35, preferably from 9 to 28, most preferably from 13 to 20.

E independently of each other represents a hydrogen atom, a substituted or unsubstituted phenyl rest, a substituted or unsubstituted heterocyclic rest, a nucleobase, optionally substituted by protecting groups, for example a naturally occurring or non-naturally occurring nucleobase, or a DNA intercalator.

Preferably, each E independently of each other represents an adeninyl, cytosinyl, pseudoisocytosinyl, guaninyl, thyminyl, uracilyl or phenyl rest.

Each rest $R^1$ independently of each other represents a hydrogen atom or an optionally substituted alkyl, alkenyl, alkylaryl, aryl, or alicyclic rest having up to 20 carbon atoms, wherein at least one rest $R^1$ does not represent a hydrogen atom and is substituted with one or more phosphonic acid ester functions or phosphonic acid functions.

If the rest $R^1$ is not substituted with one or more phosphonic acid ester functions or phosphonic acid functions, it may independently of each other also have for example one or more side chains of a naturally occurring or non-naturally occurring amino acid, and preferably, an optionally substituted alkyl, alkenyl, alkylaryl, aryl, heterocyclic or alicyclic rest having up to 20 carbon atoms.

Preferably, each rest $R^1$ independently of each other comprises 1, 2, 3, 4, 5, 6, 7, 8, 9 or 10 carbon atoms.

Each rest $R^1$ independently of each other may be branched or not branched.

The expression "optionally substituted" relates to groups in which one or more hydrogen atoms are replaced by fluorine, chlorine, bromine or iodine atoms, or by —COOH, —COOR$^8$, —CSOH, —CSOR$^8$, —COSH, —COSR$^8$, —CONH$_2$, —CONHR$^9$, —COR$^{10}$R$^{11}$, —OH, —OR$^8$, =O, —SH, —SR$^8$, =S, —NH$_2$, =NH, —NHR$^9$, —NR$^{10}$R$^{11}$, —NR$^{12}$NOH, —NOR$^{13}$ or —NO$_2$ groups, phosphonic acid ester functions or phosphonic acid functions. Furthermore, this expression relates to groups which are substituted with unsubstituted $C_1$-$C_6$ alkyl, $C_2$-$C_6$ alkenyl, $C_2$-$C_6$ alkinyl, $C_1$-$C_6$ heteroalkyl, $C_3$-$C_{10}$ cycloalkyl, $C_2$-$C_9$ heterocycloalkyl, $C_6$-$C_{10}$ aryl, $C_5$-$C_9$ heteroaryl, $C_7$-$C_{12}$ aralkyl or $C_2$-$C_{11}$ heteroaralkyl groups, wherein the rests $R^8$, $R^9$, $R^{10}$, $R^{11}$, $R^{12}$ and $R^{13}$ independently of each other represent $C_1$-$C_6$ alkyl rests.

Phosphonic acid ester functions may exhibit for example the formula —P(=O)(OV)$_2$ or —P(=O)(OV)(OH). In this context, each V independently of each other may represent an unsubstituted alkyl, alkenyl, alkylaryl, aryl, or alicyclic rest having up to 20 carbon atoms, more preferably, having up to 7 carbon atoms, and most preferably, a methyl, ethyl, cyclohexyl, or benzyl rest.

In the compounds according to the invention, the phosphonic acid functions may exhibit, for example, the formula —P(=O)(OH)$_2$.

Most preferably, each rest $R^1$ independently of each other is selected from a group of the formula —($C_1$-$C_{10}$)alkyl-[P(=O)(O—V)$_2$], wherein each V independently of each other represents a hydrogen atom, a methyl, ethyl, cyclohexyl or a benzyl rest.

K represents a group of the formula —NR$^2$R$^3$, —N$^\oplus$R$^2$R$^3$R$^4$, —NR$^2$(CO)R$^3$ or —NR$^2$(CS)R$^3$, wherein R$^2$, R$^3$ and R$^4$ independently of each other represent a hydrogen atom, an alkyl rest, an amino protecting group, reporter ligand, fluorescence marker, intercalator, chelator, amino acid, peptide, protein, carbohydrate, lipid, steroid, fatty acid, oligonucleotide, quantum dot, FRET quencher (fluorescence resonance energy transfer quencher) or a polymer soluble or insoluble in water, wherein each of the above mentioned rests optionally may be substituted.

Preferably, K represents a —NH$_2$ function, a —NH(CO)CH$_3$ rest, a group of the formula —NR$^2$R$^3$ or —N$^\oplus$R$^2$R$^3$R$^4$ or —NR$^2$(CO)R$^3$, wherein R$^2$, R$^3$ and R$^4$ independently of each other represent a hydrogen atom, each an unsubstituted amino acid, peptide or alkyl rest, or an amino acid, peptide or alkyl rest, which are each substituted with phosphonic acid ester functions or phosphonic acid functions, wherein each of the above mentioned rests may be substituted optionally.

L represents a group of the formula —NR$^5$R$^6$, —NR$^5$(CO)R$^6$, —NR$^5$(CS)R$^6$, —OR$^7$ or —SR$^7$ wherein R$^5$ and R$^6$ independently of each other represent a hydrogen atom, an alkyl rest, reporter ligand, fluorescence marker, intercalator, chelator, amino acid, amino acid amide, peptide, peptide amide, protein, carbohydrate, lipid, steroid, fatty acid, oligonucleotide, quantum dot, FRET quencher (fluorescence resonance energy transfer quencher) or a polymer soluble or insoluble in water, wherein each of the above mentioned rests optionally may be substituted, and R$^7$ represents a hydrogen atom, an alkyl rest, reporter ligand, fluorescence marker, intercalator, chelator, amino acid, amino acid amide, peptide, peptide amide, protein, carbohydrate, lipid, steroid, fatty acid, oligonucleotide, quantum dot, FRET quencher or a polymer soluble or insoluble in water, wherein each of the above mentioned rests optionally may be substituted.

Preferably, L represents a —OH function, a —NH$_2$ function, a —NH—($C_1$-$C_5$)alkyl function, an amino acid, amino acid amide, peptide or peptide amid unit, all of which may be substituted or not with phosphonic acid ester functions or phosphonic acid functions, wherein each of the above mentioned rests optionally may be substituted.

In the whole application, alkyl rests preferably may have 1-6 carbon atoms, for example, they may represent methyl, ethyl, propyl or butyl groups.

If R$^1$ does not represent a hydrogen atom, an asymmetric center (*) is generated due to the bond of the rest R$^1$ to the backbone of the general compound I at the bonding position. Therefore, at each asymmetric center, there exists an R configuration or an S configuration.

In this context, the configuration at the asymmetric center preferably is defined according to the Cahn-Ingold-Prelog rules, additionally provided that the priority of the ligands is always defined as follows: The nitrogen atom at the asymmetric center always receives priority 1. The carbon atom of the carboxyl group at the asymmetric center always receives priority 2. The carbon atom of the rest R$^1$ at the asymmetric center always receives priority 3. The hydrogen atom at the asymmetric center always receives priority 4.

In EP 1157031, oligomers are described which are exclusively prepared from racemic monomers, substituted with phosphonic acid ester functions or phosphonic acid functions. For example, for an oligomer composed of 15 racemic monomers, there are $2^{15}$ different combinations of stereogenic centers (*) or 32.768 different stereoisomers. In this case a mixture of compounds with different chemical and physical properties is obtained.

In contrast to the compounds described in EP 1157031, the presently described compounds according to the invention preferably are prepared starting from enantiomerically pure monomers, preferably substituted with one or more phosphonic acid ester functions or phosphonic acid functions.

According to the invention, the compounds of the general formula I exhibit at least two asymmetric centers, wherein at least one rest R$^1$ is substituted with one or more phosphonic acid ester functions or phosphonic acid functions.

According to a further preferred embodiment of the invention, each second rest R$^1$ independently of each other corresponds to a side chain of a naturally occurring or non-naturally occurring amino acid, preferably to an optionally substituted alkyl, alkenyl, alkylaryl, aryl, heterocyclic or alicyclic rest having up to 20 carbon atoms, and at least one rest R$^1$ represents an optionally substituted alkyl, alkenyl, alkylaryl, aryl or alicyclic rest having up to 20 carbon atoms substituted with one or more phosphonic acid ester functions or phosphonic acid functions, wherein the remaining rests R$^1$ represent hydrogen atoms.

According to a further preferred embodiment of the invention, each third rest R$^1$ independently of each other corresponds to a side chain of a naturally occurring or non-naturally occurring amino acid, preferably to an optionally substituted alkyl, alkenyl, alkylaryl, aryl, heterocyclic or alicyclic rest having up to 20 carbon atoms, and at least one rest R$^1$ represents an optionally substituted alkyl, alkenyl, alkylaryl, aryl or alicyclic rest having up to 20 carbon atoms and is substituted with one or more phosphonic acid ester functions or phosphonic acid functions, wherein the remaining rests R$^1$ represent hydrogen atoms.

According to a further preferred embodiment of the invention, two, three or more adjacent rests R$^1$ independently of each other correspond to a side chain of a naturally occurring or non-naturally occurring amino acid, preferably to an optionally substituted alkyl, alkenyl, alkylaryl, aryl, heterocyclic or alicyclic rest having up to 20 carbon atoms, and at least one rest R$^1$ represents an optionally substituted alkyl, alkenyl, alkylaryl, aryl or alicyclic rest having up to 20 carbon atoms and is substituted with one or more phosphonic acid ester functions or phosphonic acid functions, wherein the remaining rests R$^1$ represent hydrogen atoms.

According to a further preferred embodiment of the invention, each rest R$^1$ independently of each other corresponds to the side chain of a naturally occurring or non-naturally occurring amino acid, preferably to an optionally substituted alkyl, alkenyl, alkylaryl, aryl, heterocyclic or alicyclic rest having up to 20 carbon atoms, and at least one rest $R^1$ represents an optionally substituted alkyl, alkenyl, alkylaryl, aryl or alicyclic rest having up to 20 carbon atoms and is substituted with one or more phosphonic acid ester functions or phosphonic acid functions.

According to a further preferred embodiment of the invention, one or more of the rests $R^1$ independently of each other exhibit at least one phosphonic acid ester function or phosphonic acid function.

According to further preferred embodiments of the present invention, the following applies:

1. If 2 to 8 asymmetric centers and 1 to 8 optionally substituted rests $R^1$ having one or more phosphonic acid ester functions or phosphonic acid functions are present in the compound of the general formula I, at least 66% of the number of the asymmetric centers having rests with one or more phosphonic acid ester functions or phosphonic acid functions exhibit the R configuration, preferably 70%, more preferably 75%, more preferably 80%, more preferably 85%, more preferably 90%, more preferably 95%, and most preferably 100%.

2. If 9 to 36 asymmetric centers and 1 to 36 optionally substituted rests $R^1$ having one or more phosphonic acid ester functions or phosphonic acid functions are present in the compound of the general formula I, at least 70% of the number of the asymmetric centers having rests with one or more phosphonic acid ester functions or phosphonic acid functions exhibit the R configuration, more preferably 75%, more preferably 80%, more preferably 85%, more preferably 90%, more preferably 95%, and most preferably 100%.

According to alternative preferred embodiments of the present invention, the following applies:

1. If 2 to 8 asymmetric centers and 1 to 8 optionally substituted rests $R^1$ having one or more phosphonic acid ester functions or phosphonic acid functions are present in the compound of the general formula I, at least 66% of the number of the asymmetric centers having rests with one or more phosphonic acid ester functions or phosphonic acid functions exhibit the S configuration, preferably 70%, more preferably 75%, more preferably 80%, more preferably 85%, more preferably 90%, more preferably 95%, and most preferably 100%.

2. If 9 to 36 asymmetric centers and 1 to 36 optionally substituted rests $R^1$ having one or more phosphonic acid ester functions or phosphonic acid functions are present in the compound of the general formula I, at least 70% of the number of the asymmetric centers having rests with one or more phosphonic acid ester functions or phosphonic acid functions exhibit the S configuration, more preferably 75%, more preferably 80%, more preferably 85%, more preferably 90%, more preferably 95%, and most preferably 100%.

In a further embodiment, at most 50% of the number of the rests $R^1$ are substituted with phosphonic acid ester functions or phosphonic acid functions, and the remaining rests $R^1$ represent hydrogen atoms.

In a further embodiment, at most 40% of the number of the rests $R^1$ are substituted with phosphonic acid ester functions or phosphonic acid functions, and the remaining rests $R^1$ represent hydrogen atoms.

In a further embodiment, at most 30% of the number of the rests $R^1$ are substituted with phosphonic acid ester functions or phosphonic acid functions, and the remaining rests $R^1$ represent hydrogen atoms.

In a further embodiment, at most 20% of the number of the rests $R^1$ are substituted with phosphonic acid ester functions or phosphonic acid functions, and the remaining rests $R^1$ represent hydrogen atoms.

In a further embodiment, at most 10% of the number of the rests $R^1$ are substituted with phosphonic acid ester functions or phosphonic acid functions, and the remaining rests $R^1$ represent hydrogen atoms.

In a further embodiment, at most 4% of the number of the rests $R^1$ are substituted with phosphonic acid ester functions or phosphonic acid functions, and the remaining rests $R^1$ represent hydrogen atoms.

In a further preferred embodiment of the invention, all asymmetric centers (*) of the general compound I exhibit the same configuration.

In a further preferred embodiment of the invention, all asymmetric centers (*) of the general compound I exhibit the S configuration.

In a further preferred embodiment of the invention, all asymmetric centers (*) of the general compound I exhibit the R configuration.

Furthermore, compositions according to the invention are disclosed which contain one or more compounds according to the invention, optionally in combination with usual adjuvants.

The synthesis of the compounds according to the general formula I is preferably carried out from enantiomerically pure monomers. During the synthesis of the compounds of the general formula I, individual asymmetric centers may change their prior defined configuration in a small percentage due to the chemical synthesis conditions. The maximum percentage of the compounds of the general formula I formed during the synthesis is, however, stereoisomerically pure. Also these compositions are able to fulfil the object of the invention.

A compound of the general formula I may be connected through the rests K and L as linkers with a second compound of the general formula I, wherein the rests are defined as above. The configuration at the asymmetric centers of the first compound of the general formula I is independent of the configuration of the asymmetric centers of the second compound of the general formula I that is connected by the linker. Thus, for example, all asymmetric centers of the first compound of the general formula I may exhibit the R configuration, and all asymmetric centers of the second connected compound of the general formula I may exhibit the S configuration. For example, also all asymmetric centers of the first compound of the general formula I may exhibit the R configuration, and all asymmetric centers of the second connected compound of the general formula I may exhibit the R configuration.

The linker especially serves for the purpose to adjust the distance between the two compounds of the general formula I in such a way that between the two compounds of the general formula I having a linker and the single stranded RNA or DNA, or the double stranded DNA, respectively, a reciprocal interaction can take place via the respective nucleobases.

As linkers, all known linkers and all linker molecules are suitable that are applied or applicable for this purpose. For example, such a linker may represent an optionally substituted alkyl chain, a peptide, an oligonucleotide or an oligomer that is composed of at least three units of 8-amino-3,6-dioxaoctanoic acid (eg 1 units).

The substitution by a phosphonic acid ester function or a phosphonic acid function, respectively, at the rest $R^1$ in principle is responsible for the cell permeability of the compounds according to the invention. Surprisingly, the cell permeability of the compounds according to the invention is maintained or is reduced only marginally, respectively, if not a substituted rest $R^1$ is present at each of the possible positions, that is to say, if the number of the phosphonic acid ester functions or phosphonic acid functions, respectively, and therefore, the number of the asymmetric centers in the compounds according to the invention is reduced.

In this context, the good cell permeability of the compounds according to the invention is maintained in living tissue too. In an experiment Medaka fishes (Japanese killifish; Oryzias latipes) were kept for two days in a solution of the compounds according to the invention which have been marked with a fluorescence dye. Then, the fishes were transferred into fresh water in order to wash out the compounds according to the invention again out of the gastrointestinal tract the compounds of which did not penetrate into the tissue of the gastrointestinal tract. Subsequently, the fishes were investigated on different days under a fluorescence microscope. The results show that the compounds according to the invention accumulate both in the gastrointestinal tract and in the air bladder of the Medaka fishes. The penetration into the intestinal wall of the fishes could be detected also by tissue sections of the intestine. This circumstance renders the compounds according to the invention especially valuable for the treatment of diseases of the gastrointestinal tract, such as for example cancer of the colon, Morbus Crohn or for the treatment of adiposity.

The number and the sequence of the rests $R^1$ substituted with a phosphonic acid ester function or phosphonic acid function, respectively, can be freely selected according to the invention. Thus, each, each second, each third, each fourth, each fifth, each sixth, each seventh, each eighth, each ninth, or each tenth rest $R^1$, for example, may be substituted with a phosphonic acid ester function or phosphonic acid function, respectively. The substitutions with the phosphonic acid ester functions or phosphonic acid functions, respectively, can be regularly or exist at any positions.

Furthermore, also several rests $R^1$ may be substituted with a phosphonic acid ester function or phosphonic acid function, respectively, in a subsequent manner (adjacent alignment). In this context, in the compound of the general formula I, also more of these adjacent alignments may be contained.

However, for example only individual rests $R^1$ at any positions may be substituted with a phosphonic acid ester function or phosphonic acid function, respectively.

The positions with the individual subsequent rests $R^1$ substituted with a phosphonic acid ester function or phosphonic acid function, respectively, may be arbitrary.

For the compounds according to the invention, the inventors have assessed a novel principle of action at a still good cell permeability, as well as a surprisingly strong action.

In the case of the in vitro cell experiments with the compounds according to the invention, for the primary infection of host cells (first experiment) by HI viruses in the first virus daughter generation, seemingly an only slight reduction of the number of the formed viruses could be observed compared with an untreated control. This circumstance would indicate a weak antisense effect, as a person skilled in the art understands it up to now.

The number of HI viruses was investigated via a standard quantitative p24-ELISA assay since the amount of the formed viral protein p24 generally is considered as proportional to the number of the HI viruses formed.

The infectious cell medium (supernatant) of the first virus daughter generation can be isolated from the host cells by centrifugation. New host cells which have not been infected before, can be infected by this supernatant in subsequent experiments (secondary infection), wherein no further addition of the compounds according to the invention occurs. Afore, this supernatant is diluted (for example 1:5.000) in order to keep the concentration within the measurement range of the p24 assay.

In a subsequent experiment, the diluted supernatants, both those of the host cells treated with the compounds according to the invention and those of the untreated controls, are added each to host cells which have not been infected before. In this context, no further addition of the compounds according to the invention happens. Now, a strong reduction of the measured amount of p24 in the second daughter generation is obtained in the case of the treated host cells in the first experiment. In contrast thereto, the supernatant of the untreated control realizes a strong increase of the amount of p24 in the second daughter generation.

This surprising result is contradictory to the results from the first daughter generation. While seemingly an only small action is achieved in the first experiment in spite of the presence of active agent, a strong action can be seen in the subsequent experiment in the case of substantial absence of active agent.

This contradiction can only be resolved by the novel mechanism of action of the compounds according to the invention.

FIG. 1 schematically demonstrates the novel mechanism of action.

In the case of a primary infection of a host cell by a HI virus, the HI virus dismisses its viral genomic RNA into the cytosol. Subsequently, the viral DNA is transcribed into DNA by viral reverse transcriptase, and integrated into the genome of the host cell. Upon the activation of the host cell, the viral genomic RNA is formed on one hand, and viral mRNA is formed on the other hand which can be decoded into viral proteins by translation.

If the host cells are treated with the compounds according to the invention, then they are capable of permeating into the cell without further adjuvants (for example transfection reagents). In the presence of viral mRNA with a complementary sequence, the compounds according to the invention can attach to these. As a result of the attachment, the translation to distinct viral proteins is blocked. This phenomenon is called an antisense effect (1). Thereby, for example, the formation of novel viruses is interrupted (case A). For example, also the maturation of a virus particle after the burgeoning out of the host cell can be impeded by the absence of distinct viral proteins. In this case, non-infectious viruses arise (case B). Admittedly, in the p24 assay, it can not be differentiated between such non-infectious viruses, and such viruses which are still infectious. An antisense effect that is strong per se is detected in this manner falsely as a weak antisense effect.

Additionally to the mRNA (classical antisense effect), surprisingly the compounds according to the invention simultaneously also can attach to the genomic RNA having a complementary sequence (antigenomic effect) of the HI virus ($RNA^+$ virus) (2). This can happen within the host cell and/or when burgeoning.

Since the cell membrane of the virus consists of the membrane of the host cell for the most part, the compounds according to the invention, however, can permeate the membranes of the host cells also after the burgeoning of the viruses and subsequently attach to the complementary sequence of the viral genomic RNA (3).

These viruses (C and D) are still able to infect further host cells. The compounds according to the invention attached to the viral genomic RNA admittedly act as a blockade for the viral reverse transcriptase. Thereby, the transcription of RNA into DNA is no longer possible, and the replication cycle of the viruses is interrupted at this point.

Therefore, the compounds according to the invention simultaneously can attach both to complementary viral genomic RNA and to complementary viral mRNA. In the case of the attachment to the genomic RNA, the compounds according to the invention can leave the first host cell again, and permeate into a second host cell not infected before. This results in a surprising effectiveness that can be observed over two generations of viruses.

As a result of the attachment to genomic RNA, also latent viruses can be antagonized. For example, the HIV medicaments currently on the market can antagonize only replicating HI viruses. By means of a combination therapy of compounds attaching to genomic RNA (such as for example the compounds according to the invention) and compounds that keep the number of the viruses small by blocking the replication of the viruses, both replicating viruses and latent viruses simultaneously can be antagonized according to the invention, and thus, an extermination of the corresponding viruses can be achieved in the human organism.

The compounds according to the invention exhibit a superior antisense effect and a stronger effectiveness compared to the stereochemically non-uniform compounds described in EP 1157031. In both classes of compounds the intensity of the antisense effect rises with an increasing number of the monomers that have been used for the preparation of the oligomers, that is to say, with larger values of n. Even clearly shorter compounds according to the invention, however, clearly and surprisingly outclass longer, stereochemically non-uniform oligomers according to EP 1157031 in relation to the action. This property renders the compounds according to the invention especially valuable for further applications.

The compounds according to the invention are of large interest for the treatment of different diseases due to their ability to bind to complementary nucleic acid sequences. By these compounds, diseases can be antagonized which are to be attributed to the presence of DNA or RNA which is alien to the organism. For example, especially diseases are to be mentioned which are caused by viruses, for example HIV, hepatitis B and hepatitis C or HPV.

Also diseases which are to be traced back to an overexpression of body's own mRNA, can be antagonized by the compounds according to the invention. As examples, different kinds of cancer can be mentioned, such as skin cancer, lung cancer, liver cancer, prostate cancer, leukemia or brain tumors.

Corresponding experiments with compounds according to the invention showed a reduction of 33% of the cell proliferation in the breast cancer cell line MDA453 overexpressing Her2/neu. In this experiment, the cell lines were incubated in cell culture for four days with a compound according to the invention which represents a matching sequence complementary to Her2/neu mRNA. A negative control which represents no matching sequence complementary to Her2/neu mRNA showed no reduction of the cell proliferation.

The reduction of the concentration of Her2/neu in mamma carcinomas increases the survival rate in combination with conventional chemotherapeutics clearly in the case of breast cancer patients (Piccart-Gebhart M J et al.: Herceptin® Adjuvant (HERA) Trial Study Team. Trastuzumab after adjuvant chemotherapy in HER2-positive breast cancer. N. Engl. J. Med. 2005 Oct. 20; 353 (16): 1659-1672)

Furthermore, inflammation diseases, for example asthma or psoriasis, neurological diseases, for example Parkinson's disease or metabolic diseases, such as increased cholesterol values, can be antagonized by the compounds according to the invention.

Corresponding experiments with the compounds according to the invention which are directed to the expression of the cholesterol carrier protein ApoB100, showed a reduction of the content of ApoB100 of 41% in mice, compared with the control group which has been treated with PBS buffer only. Simultaneously, a reduction of ApoB48—a further cholesterol carrier protein responsible for the transport of cholesterol from colon to the liver—of 32% has been observed. The reduction of ApoB100 and ApoB48 resulted in a total reduction of the cholesterol concentration of about 25%. In this experiment, mice were administered the compounds according to the invention in a concentration of 25 mg/kg intravenously once daily at three subsequent days, and then, the blood of the mice was analyzed on the fourth day.

A reduction of ApoB100 and ApoB48 is valuable in respect of the antagonization of diseases related to arteriosclerosis and increased cholesterol values, especially in respect of high risk groups.

The use of the compounds according to the invention for the preparation of medicaments for the prevention and/or the treatment of diseases is also a subject matter of the present invention. Generally, the compounds according to the invention are administered using known and acceptable modes, either individually or in combination with any other therapeutic agent. For example, the administration can be applied by one of the following pathways: orally, for example as dragées, coated tablets, pills, semisolids, soft and hard capsules, solutions, emulsions or suspensions; parenterally, for example as injectable solution; rectally as suppositories; by inhalation, for example as a powder formulation or spray, transdermally or intranasally. For the production of such tablets, pills, semi-solids, coated tablets, dragées and hard gelatin capsules, the therapeutically useable product may be mixed with pharmacologically inert inorganic or organic drug carrier substances, for example with lactose, sucrose, glucose, gelatin, malt, silica gel, starch or derivatives thereof, talkum, stearic acid or salts thereof, and fatless powdered milk etc. For the production of soft capsules, drug carrier substances, such as vegetable oils, petroleum, animal or synthetic oils, waxes, fats, polyols, may be used. For the production of liquid solutions and sirups, drug carrier substances, such as water, alcohols, aqueous salt solution, aqueous dextrose, polyols, glycerol, vegetable oils, petroleum, animal or synthetic oils, may be used. For suppositories, drug carrier substances, such as vegetable oils, petroleum, animal or synthetic oils, waxes, fats and polyols may be used. For aerosol formulations, compressed gases suitable for this purpose, such as oxygen, nitrogen, and carbon dioxide, may be used. The pharmaceutically usable agents may also contain additives for conservation, stabilization, emulsifiers, sweeteners, flavors, salts for changing the osmotic pressure, buffer substances, additives for coating and antioxidants.

The compounds of the general formula I according to the invention may be produced for example by methods described in the literature by a reaction of compounds of the general formula II in a manner known per se (for example L. Christensen, R. Fitzpatrick, B. Gildea, K. H. Petersen, H. F. Hansen, T. Koch, M. Egholm, O. Buchardt, P. E. Nielsen, J. Coull, R. H. Berg, *J. Pept. Sci.* 3, 1995, 175-183. T. Koch, H. F. Hansen, P. Andersen, T. Larsen, H. G. Batz, K. Otteson, H. Örum, *J. Pept. Res.* 49, 1997, 80-88. F. Bergmann, W. Bannwarth, S. Tam, *Tetrahedron Lett.* 36, 1995, 6823-6826).

In the compounds of the general formula II

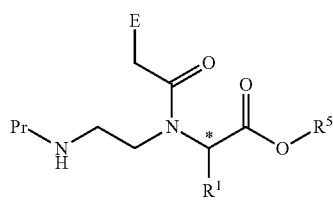

the rest $R^5$ represents for example a hydrogen atom or an allyl, benzyl, ethyl, or methyl rest, or a soluble or insoluble polymer.

Pr represents a hydrogen atom or a cleavable amine protecting group. The amine protecting group has to be selectively cleavable in the presence of the nucleobase protecting groups. Preferably, Pr represents a hydrogen atom, an oxocarbamate or thiocarbamate protecting group, most preferably, Pr represents a hydrogen atom or a Fmoc, Boc, Cbz, Mmt or a Bhoc protecting group.

E and the rest $R^1$ are as defined above.

The asymmetric center (*) which the rest $R^1$ binds to, may exhibit the R or S configuration.

For example, the compounds of the general formula II may be produced according to the following method.

Production of the compounds of the general formula II with R configuration at the asymmetric center:

Reaction Step 1:

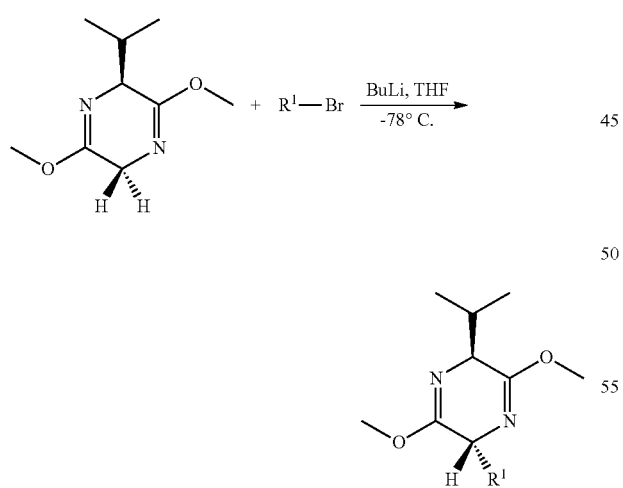

Starting from the S configuration of the pyrazine educt, the procedure may be carried out for example as described in the literature (U. Schöllkopf, U. Busse, R. Lonsky, R. Hinrichs, Liebigs Ann. Chem. 1986, 2150-2163; A. Schick, T. Kolter, A. Giannis, K. Sandhoff, Tetrahedron 51, 1995, 11207-11218).

Reaction Step 2:

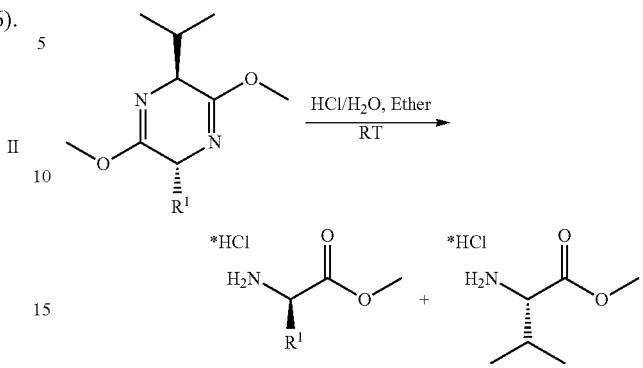

For example, the procedure can be carried out as described in the literature (U. Schöllkopf, U. Busse, R. Lonsky, R. Hinrichs, Liebigs Ann. Chem. 1986, 2150-2163).

Reaction Step 3:

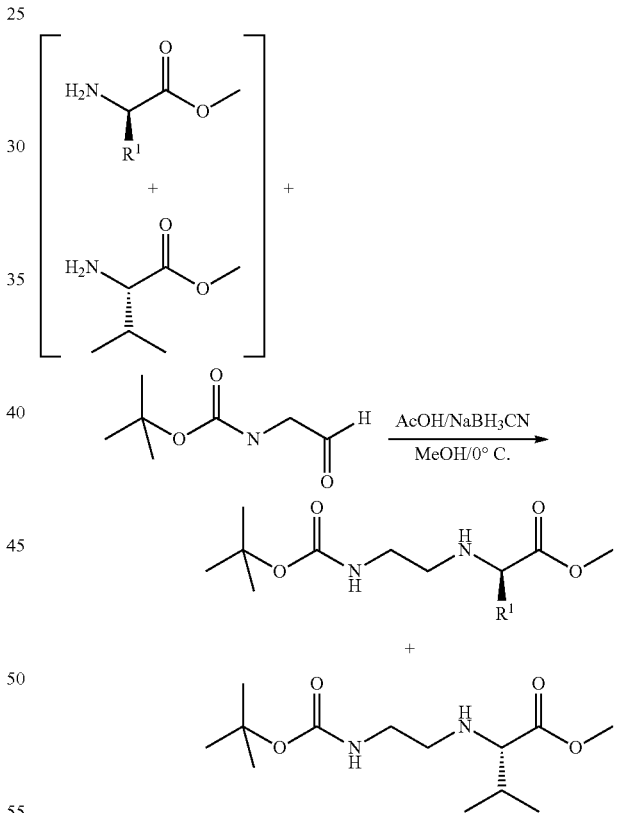

After releasing the amines from their hydrochlorides by a base (for example $NaHCO_3$, $NH_3$), the mixture of the products from reaction step 2 may be used in the following reaction. This reaction, a reductive amination, can be carried out as described in the literature (G. Haaima, A. Lohse, O. Buchardt, P. E. Nielsen, *Angew. Chem. Int. Ed. Engl.* 35, 1996, No 17, 1939-1942). Instead of sodium cyanoborohydride, also other reducing agents, for example hydrogen and a catalyst (for example Pd/C), can be used. The reaction products are separated by chromatography.

Reaction Step 4:

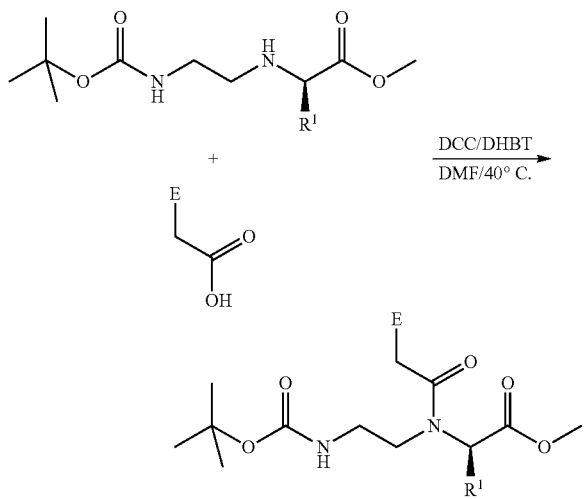

The procedure can be carried out as described in the literature (G. Haaima, A. Lohse, O. Buchardt, P. E. Nielsen, Angew. Chem. Int. Ed. Engl. 35, 1996, No 17, 1939-1942). In this context, also other coupling reagents may be used instead of DCC/DHBT. The production of the compound E-CH$_2$—COOH (for example C(PG)-CH$_2$—COOH, A(PG)-CH$_2$—COOH, G(PG)-CH$_2$—COOH, T-CH$_2$—COOH, or J(PG)-CH$_2$—COOH, wherein A=adeninyl, C=cytosinyl, G=guaninyl, T=thyminyl, J=pseudoisocytosinyl, PG=protecting group, such as benzyloxycarbonyl (Z), benzyl (Bzl), acetyl (Ac) or anisoyl (An)) can be carried out as described in the literature (S. A. Thomson, J. A. Josey, R. Cadilla, M. D. Gaul, F. C. Hassmann, M. J. Lazzio, A. J. Pipe, K. L. Reed, D. J. Ricca, R. W. Wiether, S. A. Noble, Tetrahedron 51, 1995, 6179-6194). Further possible protecting groups are also described in the literature (G. Breitpohl, D. W. Will, A. Peymann, E. Uhlmann, Tetrahedron 53, 1997, 14671-14686; T. Kofoed, H. F. Hansen, H. Orum, T. Koch, J. Peptide Sci., 7, 2001, 402-412).

Reaction Step 5:

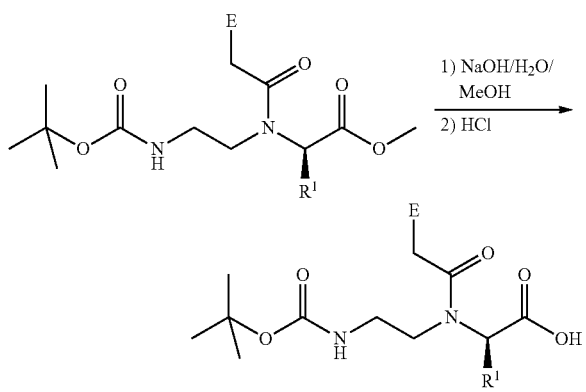

The procedure can be carried out as described in the literature (G. Haaima, A. Lohse, O. Buchardt, P. E. Nielsen, Angew. Chem. Int. Ed. Engl. 35, 1996, No 17, 1939-1942).

For a more simple description of the compounds of the general formula II which are generated as products in the reaction step 5, the following abbreviations are used: If for example A(PG)-CH$_2$—COOH is used in reaction step 4, the corresponding compound of the general formula II having an asymmetric center is obtained. This compound is abbreviated here generally as A$^R$(PG). In this context, the abbreviation A means the nucleobase in the compound of the general formula II having an asymmetric center, the raised R means the R configuration of the compound, and the abbreviation PG means the protecting group at the nucleobase. If for example phenylacetic acid is used in reaction step 4, a compound of the general formula II having an asymmetric center is obtained that is abbreviated as P$^R$.

The corresponding compounds of the general formula II without an asymmetric center (R$^1$=H) are abbreviated analogically to the compounds of the general formula II having an asymmetric center, with the difference that instead of the capital letter for the nucleobase and the raised letter for the configuration (for example A$^R$), the respective small letter a is used. For example, a compound of the general formula II without an asymmetric center having a PG protected C as nucleobase is abbreviated as c(PG).

For the production of the compounds of the general formula II having an S configuration at the asymmetric center, the pyrazine educt having an R configuration is used in reaction step 1, and the reaction steps 1 to 5 are performed analogically. Then, for example a compound of the general formula II is obtained that is abbreviated as A$^R$(PG).

The compounds according to the invention can be produced for example via solid phase synthesis by reaction of the compounds of the general formula II in a manner known per se. According to the solid phase synthesis, the protecting groups at the nucleobases are cleaved so that compounds of the general formula I are obtained which are abbreviated as follows:

For example, a compound according to the invention that is produced exclusively from compounds of the general formula II having an asymmetric center with R configuration, and that is capped with an acetyl group, is abbreviated as Ac-A$^R$G$^R$T$^R$C$^R$G$^R$T$^R$T$^R$T$^R$C$^R$A$^R$A$^R$C$^R$C$^R$—NH$_2$.

For example, a compound according to the invention that is produced from compounds of the general formula II having an asymmetric center with R configuration and from compounds of the general formula II having no asymmetric center, and that is labeled with fluorescein in the final step, and thereafter is cleaved as a primary amide from the resin, is abbreviated as Flu-A$^R$gT$^R$C$^R$G$^R$tT$^R$T$^R$T$^R$C$^R$aaC$^R$c-NH$_2$.

For example, a compound according to the invention that is produced exclusively from compounds of the general formula II having an asymmetric center with S configuration and from an L-amino acid, such as Boc-ε-(L)-trimethyl lysine iodide (Boc-ε(L)TML iodide), at a Boc-Gly-PAM-MBHA resin, and that is capped with an acetyl group in the final step, and thereafter is cleaved as a primary amide from the resin, is abbreviated as Ac-ε(L)TML-A$^S$G$^S$T$^S$C$^S$G$^S$T$^S$T$^S$T$^S$C$^S$A$^S$A$^S$C$^S$C$^S$-Gly-NH$_2$.

For example, a compound according to the invention, that is produced exclusively from compounds of the general formula II having an asymmetric center with S configuration and from four L-amino acids, such as Boc-ε-(L)-trimethyl lysine iodide (Boc-ε(L)TML iodide), at a Boc-Gly-PAM-MBHA resin, and that is capped with an acetyl group in the final step, and thereafter is cleaved as a primary amide from the resin, is abbreviated as Ac-ε(L)TML-ε(L)TML-ε(L)TML-ε(L)TML-A$^S$G$^S$T$^S$C$^S$G$^S$T$^S$T$^S$T$^S$C$^S$A$^S$A$^S$C$^S$C$^S$-Gly-NH$_2$.

For example, a compound according to the invention that is produced from compounds of the general formula II having an asymmetric center with R configuration and from compounds of the general formula II having no asymmetric center, from glycine, and from two amino acids, such as 4-(diethoxy-phosphoryl)-2-(tert.-butoxycarbonylamino)butyric acid (Boc-DEPABS), at a Boc-Gly-PAM-MBHA resin, and that is capped with an acetyl group in the final step, and thereafter is cleaved as a primary amide from the resin, is abbreviated as Ac-(DEPABS)-2-Gly-gcgtG$^R$tG$^R$ggaagG$^R$-cA$^R$g-Gly-NH$_2$.

For example, a compound according to the invention that is produced from compounds of the general formula II having an asymmetric center with R configuration and from compounds of the general formula II having no asymmetric center, from the amino acids L-lysine (L-Lys), L-arginine (L-Arg), L-valine, (L-Val), at a Boc-Gly-PAM-MBHA resin, and that is capped with an acetyl group in the final step, and thereafter is cleaved as a primary amide from the resin, is abbreviated as Ac-(L-Lys)-(L-Lys)-(L-Lys)(L-Arg)-(L-Lys)-(L-Val)-agctC$^R$cT$^R$cgcccT$^R$tG$^R$c-Gly-NH$_2$.

For example, a compound according to the invention that is produced from compounds of the general formula II having an asymmetric center with R configuration, from compounds of the general formula II having no asymmetric center, and from the amino acids Boc-ϵ-(L)-trimethyl lysine iodide (Boc-ϵ(L)TML iodide) and from the chelator 1,4,7,10-tetraazacyclododecane-1,4,7,10-tetraacetic acid tri-tert. butyl ester (DOTA), at a Boc-Gly-PAM-MBHA resin, and thereafter is cleaved as a primary amide from the resin, is abbreviated as DOTA-ϵ(L)TML-C$^R$aG$^R$tT$^R$aG$^R$gG$^R$tT$^R$aG$^R$-Gly-NH$_2$.

BRIEF DESCRIPTION OF THE DRAWINGS

The embodiments of the invention described herein may be understood in conjunction with accompanying Figures, in which:

FIG. 5 shows fluorescence microscopic photographs of the localization of the compounds according to the invention in the gastrointestinal tract and the air bladder of Medaka fishes on days 1 (above photo), 2 (middle photo), and 5 (bottom photo) after transfer into fresh water.

EXAMPLES

Figure 1:
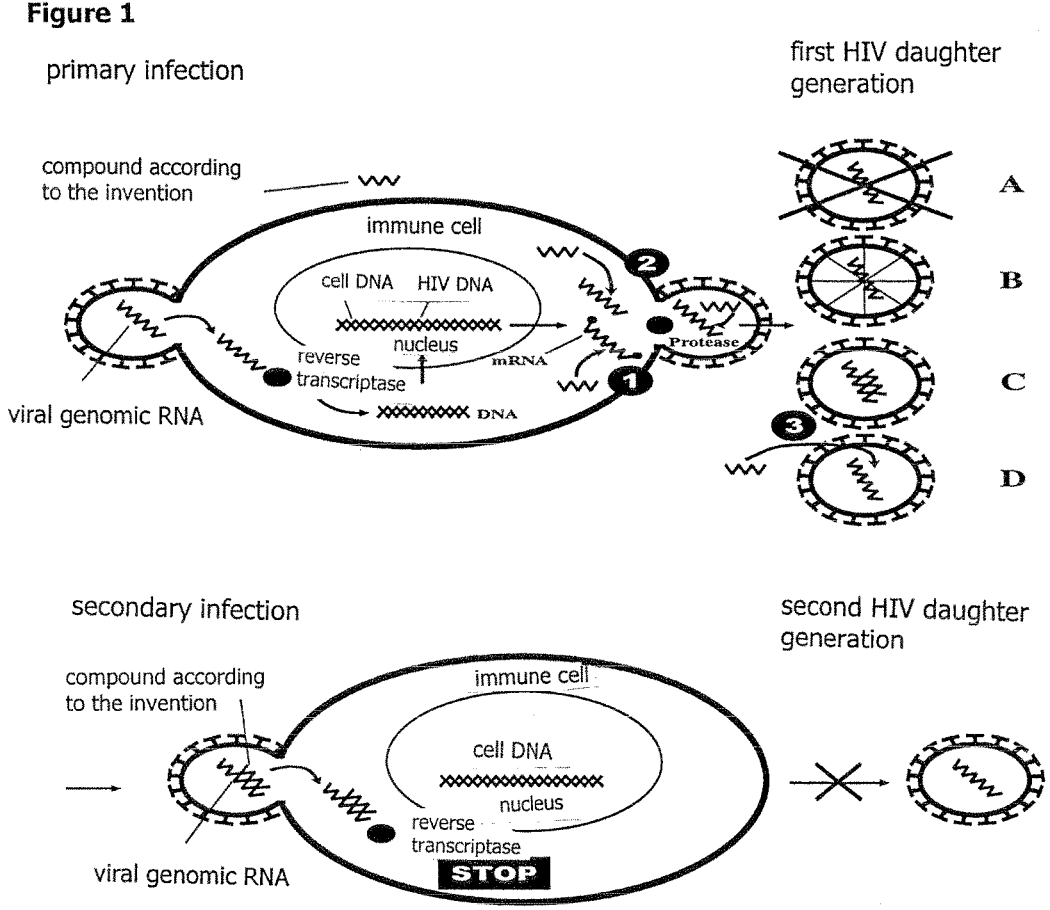
FIG. 1 is a schematic of the mechanism of action according to embodiments of the invention in primary infection (above scheme) and secondary infection (bottom scheme).

Example 1: Production of (2R,5S)-2-(2-(diethoxy-phosphoryl)ethyl)-2,5-dihydro-3,6-dimethoxy-5-isopropyl pyrazine

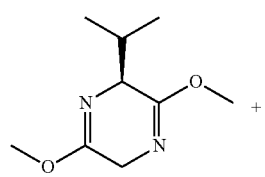

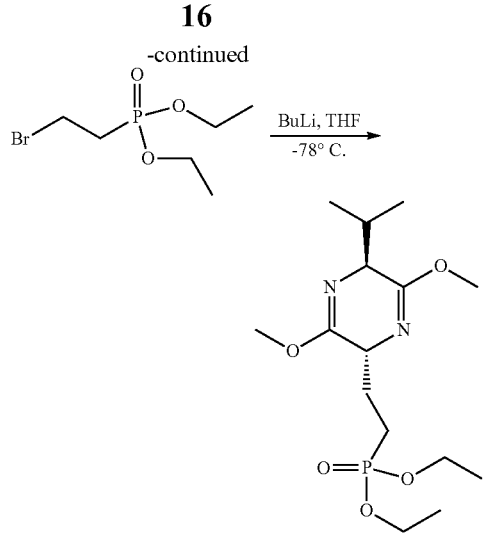

0.52 mol of (S)-2,5-dihydro-3,6-dimethoxy-2-isopropyl pyrazine are solved in 400 ml of absolute THF under argon and are cooled to −78° C. Under stirring, 200 ml of a 2.7 M solution of butyl lithium (in heptane) (0.54 mol) are added in drops and slowly. Subsequently, a solution of 0.52 mol of diethyl-(2-bromoethyl)phosphonate in 300 ml of absolute THF is added in drops and slowly during stirring, and the mixture is stirred for further 3 h at −78° C. Then, 11.7 ml (about 0.2 mol) anhydrous acetic acid are added slowly. The reaction mixture is allowed to warm up slowly to room temperature. The solvent is removed, and the residue is solved in 600 ml of diethyl ether and washed with 200 ml of water. The aqueous phase is still extracted three times with each 100 ml of diethyl ether. The combined ether phases are dried over MgSO$_4$, filtered and the solvent is removed in vacuo. The residue is solved in a mixture of diethyl ether and hexane (1:10) and filtered over a bed of silica gel. Thereby, first it is eluted with diethyl ether and hexane (1:5).

Yield: about 70% of a yellow liquid.

$^1$H-NMR (CDCl$_3$): 0.71, 1.04 (d, 6H, CH(CH$_3$)$_2$), 1.33 (t, 6H, P(O)(OCH$_2$CH$_3$)$_2$), 1.68-2.25 (m, 4H, CHCH$_2$CH$_2$P), 3.65, 3.67 (s, 6H, OCH$_3$), 4.02 (m, 1H), 4.10-4.20 (m, 4H, P(O)(OCH$_2$CH$_3$)$_2$).

Example 2: Production of (2R,5S)-2-(8-(dibenzyloxy-phosphoryl)octyl)-2,5-dihydro-3,6-dimethoxy-5-isopropyl pyrazine Analogically to the production method in example 1, (2R,5S)-2-(8-dibenzyloxyphosphoryl)octyl)-2,5-dihydro-3,6-dimethoxy-5-isopropyl pyrazine is produced starting from (S)-2,5-dihydro-3,6-dimethoxy-2-isopropyl pyrazine and dibenzyl-(8-bromooctyl)phosphonate.

Example 3: Production of (2S,5R)-2-(4-(dicyclohexyloxy-phosphoryl)but-2-enyl)-2,5-dihydro-3,6-dimethoxy-5-isopropyl pyrazine Analogically to the production method in example 1, (2S,5R)-2-(4-(dicyclohexyloxyphosphoryl)but-2-enyl)-2,5-dihydro-3,6-dimethoxy-5-isopropyl pyrazine is produced starting from (R)-2,5-dihydro-3,6-dimethoxy-2-isopropyl pyrazine and dicyclohexyl-(4-bromo-but-2-enyl)phosphonate.

Example 4: Production of (2R)-2-[2-(tert.-butoxy-carbonyl amino)ethyl]-amino-4-(diethoxy-phosphoryl)butyric acid methyl ester

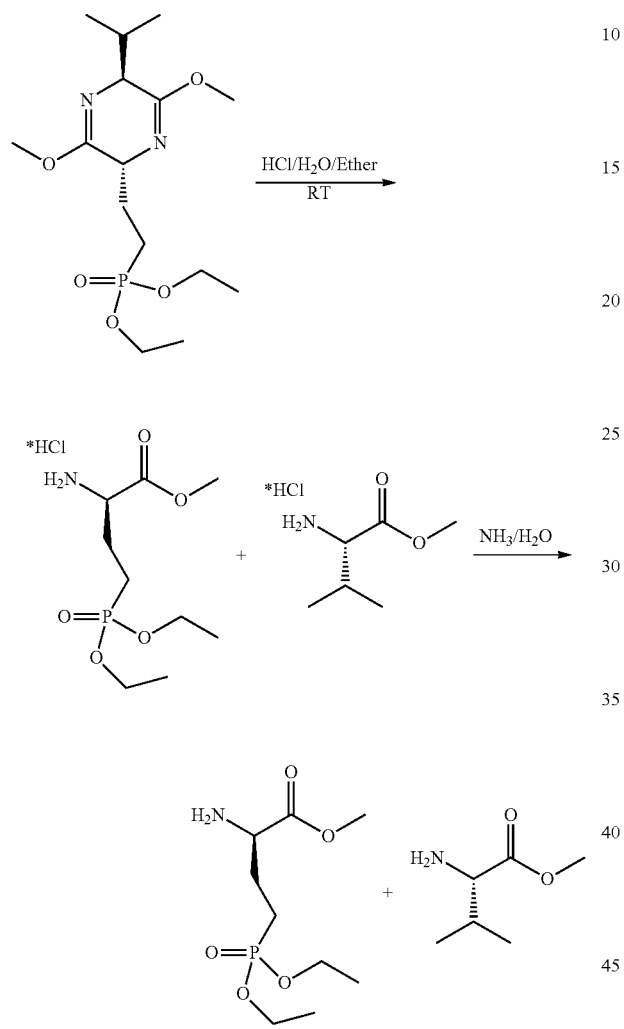

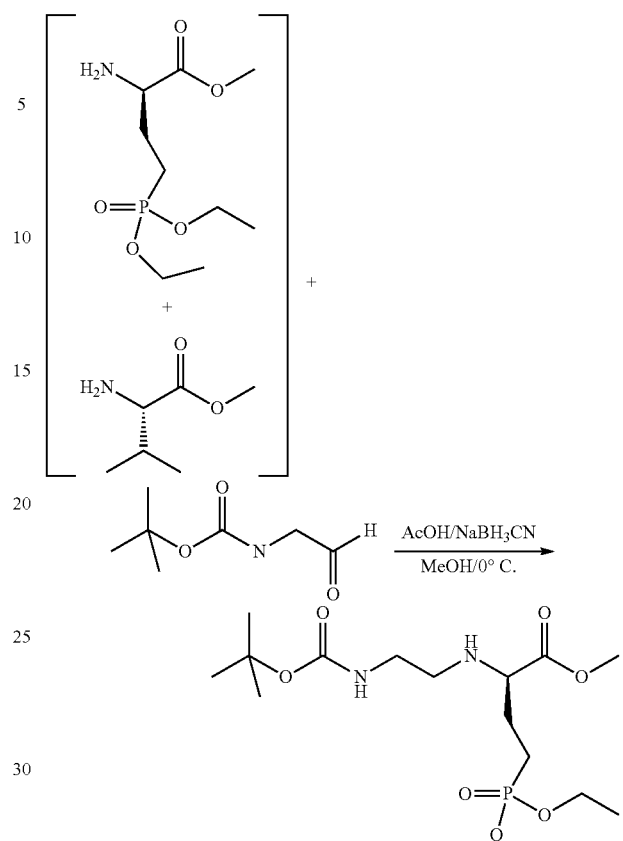

0.38 mol of (2R,5S)-2-(2-(diethoxy-phosphoryl)ethyl)-2,5-dihydro-3,6-dimethoxy-5-isopropyl pyrazine are solved in 400 ml of diethyl ether. To this solution, 1150 ml of a 1 N aqueous solution of hydrochloric acid are added. After 60 min, the reaction is completed and the ether is removed. If the product is to be stored, the water is also completely removed in vacuo. If the product is to be further reacted immediately, about one half of the water is removed by a rotating evaporator, and then, the pH value of the reaction mixture is adjusted to 8-9 by ammonia solution. The basic solution is extracted six times with dichloromethane, wherein the pH value is controlled and optionally corrected each time. The dichloromethane phases are combined, dried over MgSO$_4$, and the solvent is removed in vacuo. The resulting yellow oil is immediately used in the following reaction, an reductive amination.

The yellow oil (a complete reaction is assumed) is solved in 600 ml of methanol and cooled to 0° C. Subsequently, 0.76 mol of N-Boc-amino acetaldehyde are added. After stirring for 30 min at 0° C., at first 0.90 mol of anhydrous acetic acid and then 0.40 mol of sodium cyanoborohydride are added. The reaction mixture is stirred at 0° C., until the generation of gas is completed, and then the solvent is removed by a rotating evaporator. The residue is solved in acetic acid ethyl ester (about 600 ml), and further, washed once with saturated sodium bicarbonate solution (about 200 ml) and once with saturated sodium chloride solution (about 100 ml). The organic phase is dried over MgSO$_4$ and filtered. Subsequently, the solvent is removed in vacuo.

The further purification is carried out by SPE over a glass frit filled with silica gel. Impurities and unwanted products are at first eluted with a mixture of hexane and acetic acid ethyl ester (1:1), and then with pure acetic acid ethyl ester. The desired product is finally obtained by extraction with 10% methanol in dichloromethane.

After removing the solvent, about 75% of the product are obtained as a yellow viscous oil.

$^1$H-NMR (CDCl$_3$): 1.35 (t, 6H, P(O)(OCH$_2$CH$_3$)$_2$), 1.47 (s, 9H, C(CH$_3$)$_3$); 1.8-2.0 (m, 4H, CHCH$_2$CH$_2$P), 2.5-2.6, 2.75-2.85, 3.0-3.4 (m, 4H, NCH$_2$CH$_2$N), 3.75 (s, 3H, OCH$_3$), 4.0-4.2 (m, 4H, P(O)(OCH$_2$CH$_3$)$_2$).

Example 5: Production of (2R)-2-[2-(tert.-butoxycarbonylamino)ethyl]-amino-10-(dibenzyloxy-phosphoryl)decanoic acid methyl ester Analogically to the production method in example 4, (2R)-2-[2-(tert.-butoxycarbonylamino)ethyl]-amino-10-(dibenzyloxy-phosphoryl)-decanoic acid methyl ester is produced starting from (2R,5S)-2-(8-(dibenzyloxy-phosphoryl) octyl)-2,5-dihydro-3,6-dimethoxy-5-isopropyl pyrazine.

Example 6: Production of (2S)-2-[2-(tert.-butoxycarbonylamino)ethyl]-amino-6-(dicyclohexyloxyphosphoryl)hex-4-enoic acid methyl ester Analogically to the production method in example 4, (2S)-2-[2-(tert.-butoxycarbonylamino)ethyl]-amino-6-(dicyclohexyloxy-phosphoryl)-hex-4-enoic acid methyl ester is produced starting from (2S,5R)-2-(4-(dicyclohexyloxyphosphoryl)-but-2-enyl)-2,5-dihydro-3,6-dimethoxy-5-isopropyl pyrazine.

Example 7: Production of (R)-2-([2-{N4-benzyloxycarbonylcytosin-1-yl}-acetyl]-[2-tert.-butoxycarbonylaminoethyl]-amino)-4-(diethoxy-phosphoryl)butyric acid methyl ester

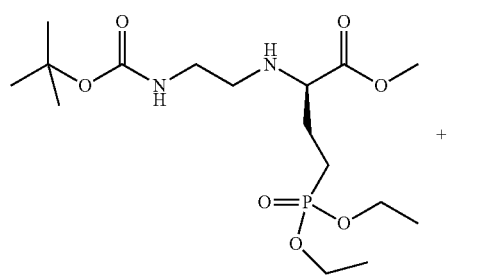

+

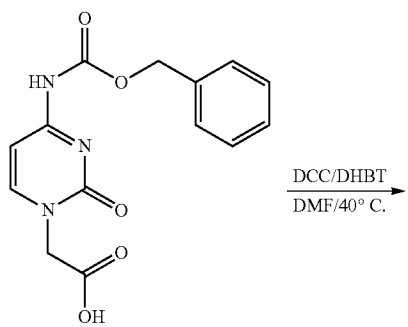

DCC/DHBT
―――――――→
DMF/40° C.

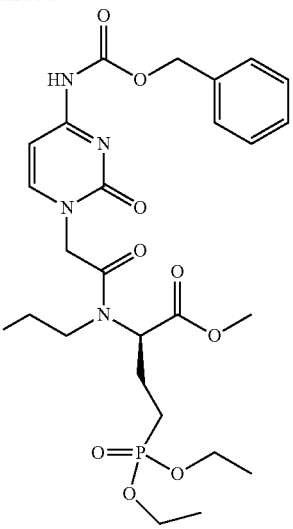

To a stirred solution of 30.96 mmol of 4-N-(benzyloxycarbonyl)-cytosin-1-yl-acetic acid and 30.96 mmol of 3,4-dihydro-3-hydroxy-4-oxo-1,2,3-benzotriazine (DHBT-OH) in 100 ml of absolute DMF, 32.51 mmol of dicyclohexyl carbodiimide are added, and this solution is stirred for 1 h at 40° C. Subsequently, 23.84 mmol of (2R)-2-[2-(tert.butoxycarbonylamino)ethyl]-amino-4-(diethoxy-phosphoryl) butyric acid methyl ester are added and stirred at 40° C. The reaction is monitored by HPLC and is completed after 3 days.

The solution is separated from insoluble parts by filtration, and the solvent is removed in vacuo. The residue is solved in dichloromethane and is stored overnight in a refrigerator. In this process, further dicyclohexyl urea precipitates which is separated by filtration. The filtrate is washed two or three times with diluted sodium bicarbonate solution (1/3 saturated sodium bicarbonate solution, 2/3 water), one or two times with diluted potassium hydrogen sulfate solution (1/3 saturated potassium hydrogen sulfate solution, 2/3 water), dried over MgSO$_4$ and concentrated by means of a rotating evaporator. The further purification is carried out by solving in acetic acid ethyl ester and storing overnight in the refrigerator, whereupon further optionally precipitated dicyclohexyl urea is separated by filtration and the solvent is removed again. The crude product is then solved in dichloromethane (5 ml per 3 g crude product respectively), and again precipitated with diethyl ether (25 ml per 3 g crude product respectively) and hexane (5 ml per 3 g crude product respectively). The solvent with the impurities is removed and the product is dried in vacuo.

Yield: about 65% of a bright yellow solid $^1$H-NMR (CDCl$_3$): 1.32 (t, 6H, P(O)(OCH$_2$CH$_3$)$_2$); 1.44 (s, 9H, C(CH$_3$)$_3$); 1.75-2.45 (m, 4H, CHCH$_2$CH$_2$P); 3.2-3.85 (m, 4H, NCH$_2$CH$_2$N); 3.73 (s, 3H, OCH$_3$); 4.07 (m, 4H, P(O)(OCH$_2$CH$_3$)$_2$); 4.28 (m, 1H, NCHC(O)); 4.42/4.99 (2d, 2H, NCH$_2$C(O)); 5.22 (s, 2H, OCH$_2$Ph); 5.56 (t, br, 1H, C(O)NHCH$_2$); 7.25 (d, 1H, CCH=CHN); 7.38 (s, 5H, Ph); 7.55 (d, 1H, CCH=CHN).

Example 8: Production of (R)-2-([2-{N4-benzyloxycarbonylamino-cytosin-1-yl}-acetyl]-[2-tert.-butoxycarbonylamino-ethyl]-amino)-4-(diethoxyphosphoryl)butyric acid

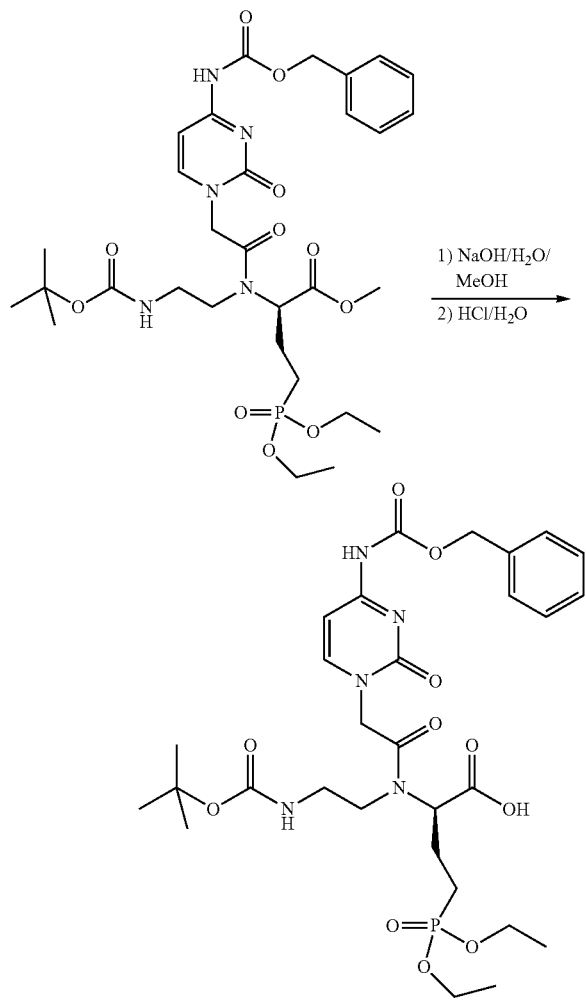

19.1 mmol of (R)-2-([2-{N4-benzyloxycarbonylcytosin-yl}-acetyl]-[2-tert.-butoxycarbonylamino-ethyl]-amino)-4-(diethoxy-phosphoryl) butyric acid methyl ester are solved in 80 ml of THF and water (2:3) and cooled to 0° C. To this solution, 48 ml of a 1 M solution of lithium hydroxide are added in drops (pH~9). The progress of the reaction is monitored by means of DC (10% methanol in dichloromethane). After completion of the reaction, the reaction solution is diluted with 130 ml water and sodium chloride solution and once extracted with dichloromethane (200 ml). The aqueous phase is adjusted with 2 M potassium hydrogen sulfate solution to a pH value of 2-3, and several times extracted with dichloromethane. Thereby, the pH value is controlled and optionally corrected again and again. The combined organic phases are dried over $MgSO_4$, and the solvent is removed in vacuo. If necessary, the crude product can be reprecipitated from dichloromethane with diethyl ether. Finally, the product is dried by a lyophylisator.

Yield: about 80% of a white yellow solid $^1$H-NMR (DMSO-$d_6$): 1.21 (t, 6H, P(O)(OCH$_2$CH$_3$)$_2$); 1.39 (s, 9H, C(CH$_3$)$_3$); 1.70-2.30 (m, 4H, CHCH$_2$CH$_2$P); 2.90-3.60 (m, 4H, NCH$_2$CH$_2$N); 3.93-4.02 (m, 4H, P(O)(OCH$_2$CH$_3$)$_2$); 4.25 (m, 1H, NCHC(O)); 4.50-4.83 (m, 2H, NCH$_2$C(O)); 5.19 (s, 2H, OCH$_2$Ph); 6.88 (m, br, 1H, C(O)NHCH$_2$); 7.02 (d, 1H, CCH=CHN); 7.31-7.41 (m, 5H, Ph); 7.97 (d, 1H, CCH=CHN).

Example 9: Production of Further Compounds of the General Formula II

By analogous syntheses as described in the examples 7 and 8, wherein in addition to C(Z)—CH$_2$—COOH further Z protected, benzyl protected (Bzl), anisoyl protected (An) or acetyl protected (Ac), respectively, and unprotected nucleobase acetic acid components, such as A(Z)—CH$_2$—COOH, A(An)-CH$_2$—COOH, A(Bzl)-CH$_2$—COOH, or G(Z)—CH$_2$—COOH, G(Ac)—CH$_2$—COOH, C(An)-CH$_2$—COOH, C(Bzl)-CH$_2$—COOH, J(Z)—CH$_2$—COOH, J(Bzl)-CH$_2$—COOH, J(An)-CH$_2$—COOH or T-CH$_2$—COOH, respectively, (A=adeninyl, C=cytosinyl, G=guaninyl, T=thyminyl; J=pseudoisocytosinyl) as well as phenylacetic acid are used, further compounds of the general formula II according to the invention are produced.

$A^R$(Z):
$^1$H-NMR (CH$_3$OH-$d_4$): 1.20 (t, 6H, P(O)(OCH$_2$CH$_3$)$_2$); 1.34 (s, 9H, C(CH$_3$)$_3$); 1.70-2.30 (m, 4H, CHCH$_2$CH$_2$P); 3.00-3.80 (m, 4H, NCH$_2$CH$_2$N); 3.93-4.02 (m, 4H, P(O)(OCH$_2$CH$_3$)$_2$); 4.10 (m, 1H, NCHC(O)); 5.18 (s, 2H, OCH$_2$Ph); 5.20-5.40 (m, 2H, NCH$_2$C(O)); 7.15-7.40 (m, 5H, Ph); 8.14 (s, 1H, N=CHN); 8.46 (s, 1H, N=CHN).

$A^R$(BZl):
$^1$H-NMR (DMSO-$d_6$): 1.21 (t, 6H, P(O)(OCH$_2$CH$_3$)$_2$), 1.40 (s, 9H, C(CH$_3$)$_3$); 1.70-2.20 (m, 4H, CHCH$_2$CH$_2$P), 2.90-3.75 (m, 4H, NCH$_2$CH$_2$N); 3.90-4.10 (m, 4H, P(O)(OCH$_2$CH$_3$)$_2$); 4.22 (m, 1H, NCHC(O)); 5.25-5.45 (m, 2H, NCH$_2$C(O)); 6.96 (m, br, 1H, C(O)NHCH$_2$); 7.50-8.10 (m, 5H, Ph); 8.42 (s, 1H, N=CHN); 8.69 (s, 1H, N=CHN).

$A^R$(An):
$^1$H-NMR (DMSO-$d_6$): 1.21 (t, 6H, P(O)(OCH$_2$CH$_3$)$_2$); 1.41 (s, 9H, C(CH$_3$)$_3$); 1.70-2.20 (m, 4H, CHCH$_2$CH$_2$P); 2.90-3.750 (m, 4H, NCH$_2$CH$_2$N); 3.86 (s, 3H, OCH$_3$); 3.90-4.10 (m, 4H, P(O)(OCH$_2$CH$_3$)$_2$); 4.22 (m, 1H, NCHC(O)); 5.25-5.45 (m, 2H, NCH$_2$C(O)); 6.96 (m, br, 1H, C(O)NHCH$_2$); 7.08 (d, 2H, Ph); 8.05 (d, 2H, Ph); 8.42 (s, 1H, N=CHN); 8.69 (s, 1H, N=CHN).

$J^R$(Z):
$^1$H-NMR (DMSO-$d_6$): 1.32 (t, 6H, P(O)(OCH$_2$CH$_3$)$_2$), 1.42 (s, 9H, C(CH$_3$)$_3$); 1.60-2.50 (m, 4H, CHCH$_2$CH$_2$P), 3.10-3.55 (m, 4H, NCH$_2$CH$_2$N); 3.65-3.90 (m, 2H, NCH$_2$C(O)); 4.00-4.15 (m, 4H, P(O)(OCH$_2$CH$_3$)$_2$); 4.20 (m, 1H, NCHC(O)); 5.24 (s, 2H, OCH$_2$Ph); 6.80 (m, br, 1H, C(O)NHCH$_2$); 7.27 (d, 1H, C=CHN); 7.30-7.50 (m, 5H, Ph).

$J^R$(An):
$^1$H-NMR (DMSO-$d_6$): 1.22 (t, 6H, P(O)(OCH$_2$CH$_3$)$_2$); 1.38 (s, 9H, C(CH$_3$)$_3$); 1.65-2.25 (m, 4H, CHCH$_2$CH$_2$P); 2.80-3.70 (m, 4H, NCH$_2$CH$_2$N); 2.80-3.70 (m, 2H, CCH$_2$C(O)); 3.84 (s, 3H, OCH$_3$); 3.90-4.05 (m, 4H, P(O)(OCH$_2$CH$_3$)$_2$); 4.17 (m, 1H, NCHC(O)); 6.81 (m, br, 1H, C(O)NHCH$_2$); 7.05 (d, 2H, Ph); 7.70 (s, 1H, NCH=C); 8.07 (d, 2H, Ph).

$G^R$(Z):
$^1$H-NMR (DMSO-$d_6$): 1.18 (t, 6H, P(O)(OCH$_2$CH$_3$)$_2$), 1.37 (s, 9H, C(CH$_3$)$_3$); 1.70-2.30 (m, 4H, CHCH$_2$CH$_2$P); 2.95-3.70 (m, 4H, NCH$_2$CH$_2$N); 3.90-4.10 (m, 4H, P(O)(OCH$_2$CH$_3$)$_2$); 4.20 (m, 1H, NCHC(O)); 4.85-5.20 (m, 2H, NCH$_2$C(O)); 5.269 (s, 2H, OCH$_2$Ph); 6.95 (m, br, 1H, C(O)NHCH$_2$); 7.30-7.50 (m, 5H, Ph); 7.85 (s, 1H, N=CHN).

$G^R(AC)$:

$^1$H-NMR (DMSO-d$_6$): 1.20 (t, 6H, P(O)(OCH$_2$CH$_3$)$_2$); 1.41 (s, 9H, C(CH$_3$)$_3$); 1.70-2.18 (m, 4H, CHCH$_2$CH$_2$P); 2.20 (s, 3H, CH$_3$C(O)); 2.90-3.60 (m, 4H, NCH$_2$CH$_2$N); 3.90-4.10 (m, 4H, P(O)(OCH$_2$CH$_3$)$_2$); 4.22 (m, 1H, NCHC(O)); 4.91-5.22 (m, 2H, NCH$_2$C(O)); 7.00 (m, br, 1H, C(O)NHCH$_2$); 7.88 (s, 1H, N=CH—N).

$C^R$(Bzl):

$^1$H-NMR (DMSO-d$_6$): 1.21 (t, 6H, P(O)(OCH$_2$CH$_3$)$_2$); 1.40 (s, 9H, C(CH$_3$)$_3$); 1.70-2.30 (m, 4H, CHCH$_2$CH$_2$P); 3.20-3.60 (m, 4H, NCH$_2$CH$_2$N); 3.93-4.02 (m, 4H, P(O)(OCH$_2$CH$_3$)$_2$); 4.28 (m, 1H, NCHC(O)); 4.50-4.83 (m, 2H, NCH$_2$C(O)); 6.90 (m, br, 1H, C(O)NHCH$_2$); 7.33 (d, 1H, CCH=CHN); 7.50-7.55 (m, 2H, Ph); 7.62 (d, 1H, CCH=CHN); 8.00-8.10 (m, 3H, Ph).

$C^R$(An):

$^1$H-NMR (DMSO-d$_6$): 1.22 (t, 6H, P(O)(OCH$_2$CH$_3$)$_2$); 1.39 (s, 9H, C(CH$_3$)$_3$); 1.65-2.10 (m, 4H, CHCH$_2$CH$_2$P); 3.20-3.60 (m, 4H, NCH$_2$CH$_2$N); 3.84 (s, 3H, OCH$_3$); 3.85-4.05 (m, 4H, P(O)(OCH$_2$CH$_3$)$_2$); 4.25 (m, 1H, NCHC(O)); 4.50-4.95 (m, 2H, NCH$_2$C(O)); 6.90 (m, br, 1H, C(O)NHCH$_2$); 7.04 (d, 2H, Ph); 7.30 (d, 1H, CCH=CHN); 8.00 (d, 1H, CCH=CHN); 8.03 (d, 2H, Ph).

$T^R$:

$^1$H-NMR (DMSO-d$_6$): 1.22 (t, 6H, P(O)(OCH$_2$CH$_3$)$_2$); 1.39 (s, 9H, C(CH$_3$)$_3$); 1.65-2.20 (m, 4H, CHCH$_2$CH$_2$P); 1.75 (s, 3H, C≡CCH$_3$); 2.90-3.50 (m, 4H, NCH$_2$CH$_2$N); 3.90-4.10 (m, 4H, P(O)(OCH$_2$CH$_3$)$_2$); 4.18 (m, 1H, NCHC(O)); 4.45-4.65 (m, 2H, NCH$_2$C(O)); 6.86 (m, br, 1H, C(O)NHCH$_2$); 7.37 (s, 1H, NCH=C).

$P^R$:

$^1$H-NMR (DMSO-d$_6$): 1.20 (t, 6H, P(O)(OCH$_2$CH$_3$)$_2$); 1.38 (s, 9H, C(CH$_3$)$_3$); 1.46-2.30 (m, 4H, CHCH$_2$CH$_2$P); 3.00-3.45 (m, 4H, NCH$_2$CH$_2$N); 3.50-3.75 (m, 2H, CCH$_2$C(O)); 3.80-4.00 (m, 4H, P(O)(OCH$_2$CH$_3$)$_2$); 4.22 (m, 1H, NCHC(O)); 7.10-7.30 (m, 5H, Ph).

Example 10: Production of Further Compounds of the General Formula II Having an S Configuration at the Asymmetric Center The production method for the compounds of the general formula II having an R configuration is applied analogically to the production of the corresponding compounds of the general formula II having an S configuration. Here, (R)-2,5-dihydro-3,6-dimethoxy-2-isopropyl pyrazine is used as a starting material in the synthesis described in example 1, and the following syntheses are carried out analogically as described.

$J^S$(Z):

$^1$H-NMR (DMSO-d$_6$): 1.32 (t, 6H, P(O)(OCH$_2$CH$_3$)$_2$), 1.42 (s, 9H, C(CH$_3$)$_3$); 1.60-2.50 (m, 4H, CHCH$_2$CH$_2$P), 3.10-3.55 (m, 4H, NCH$_2$CH$_2$N); 3.65-3.90 (m, 2H, NCH$_2$C(O)); 4.00-4.15 (m, 4H, P(O)(OCH$_2$CH$_3$)$_2$); 4.20 (m, 1H, NCHC(O)); 5.24 (s, 2H, OCH$_2$Ph); 6.80 (m, br, 1H, C(O)NHCH$_2$); 7.27 (d, 1H, C=CHN); 7.30-7.50 (m, 5H, Ph).

Example 11: General Synthesis Specification for Compounds According to the Invention By sequential connection of corresponding compounds of the general formula II having an asymmetric center and/or corresponding compounds of the general formula II having no asymmetric center and/or amino acids and/or amino acid derivatives and/or fluorescence markers by means of solid phase peptide synthesis, the compounds according to the invention are produced.

In this context, the following synthesis protocol is applied:

Step 1: 3 h Preswelling of 10 mg of resin (Boc-Gly-PAM-MBHA resin, 0.54 mmol/g) in dichloromethane.

Step 2: Start of the synthesis cycle: 4× washing with dichloromethane.

Step 3: Cleavage of the Boc group by reaction with TFA and m-cresol (95:5). Reaction period: 2×3 min in each case.

Step 4: 5× Washing with dichloromethane.

Step 5: 5× Washing with NMP.

Step 6: 1 min Preactivation of 4 equivalents of the corresponding protected compound of the general formula II, or of a correspondingly protected amino acid, respectively, with 3.8 equivalents of HATU and 9 equivalents of NMM in NMP and pyridine (2:1).

Step 7: Reaction of the activated protected compound of the general formula II, or of a correspondingly protected amino acid, respectively, with the solid phase; (1. coupling; period of time: 30 min).

Step 8: 4× Washing with NMP.

Step 9: 1× Washing with dichloromethane.

Step 10: Repetition of steps 6 to 8 (2. coupling).

Step 11: Examination of the efficiency of the coupling with ninhydrin (Kaiser's test; if the Kaiser's test shows a positive result, the steps 6 to 8 have to be repeated with the corresponding protected compound of the general formula II).

Step 12: After a negative Kaiser's test, the reaction sequence is capped two times with a solution of Ac$_2$O, NMP and pyridin (1:15:25) for 4 min in each case.

Step 13: 5× Washing with NMP.

Step 14: Repeating of the synthesis cycles (steps 2 to 13) up to the coupling with the final corresponding protected compound of the general formula II. Subsequently, the synthesis cycles are optionally repeated (steps 2 to 13) up to the coupling with the final correspondingly protected amino acid.

Step 15: After the coupling of the final corresponding protected compound of the general formula II, or of a correspondingly protected amino acid, respectively, the steps 2 to 5 for the final cleavage of the Boc group and the steps 12 and 13 (without a preceding Kaiser's test) are performed for final capping.

Step 16: 5× Washing with dichloromethane.

Step 17: For drying: 5× washing with diethyl ether.

A compound of the general formula I is obtained that is bound to the resin at the carboxylic acid terminal end.

Cleavage of the compound according to the invention from the resin:

The resin with the compound according to the invention is stirred in an aqueous ammonia solution (28-30 weight percent NH$_3$ in H$_2$O) at 60° C. for 20 h. The cleaved resin is subsequently filtered, and the filtrate is concentrated in vacuo and dried. The crude product is purified by preparative HPLC over a RP-C18 column with methanol and water. The compound according to the invention is obtained as a colorless solid in a yield of about 50%. The molecular weight of the compound according to the invention is characterized by MALDI-TOF.

Example 12: General Synthesis Specification for Compounds According to the Invention with a Linker By sequential connection of compounds of the general formula II, or of commercially available unprotected or Z-protected compounds of the general formula II without an asymmetric center, respectively, or of amino acids as well as of suitable linker monomers by means of solid phase peptide synthesis, the compounds according to the invention having a linker are produced.

Synthesis Protocol:

Step 1: 3 h Preswelling of 10 mg resin (Boc-Gly-PAM-MBHA resin, 0.54 mmol/g) in dichloromethane.

Step 2: Start of the synthesis cycle: 4× washing with dichloromethane.

Step 3: Cleavage of the Boc group by reaction with TFA and m-cresol (95:5). Reaction period: 2×3 min in each case.

Step 4: 5× Washing with dichloromethane.

Step 5: 5× Washing with NMP.

Step 6: 1 min Preactivation of 4 equivalents of the corresponding protected compound of the general formula II, or of a correspondingly protected amino acid, respectively, with 3.8 equivalents of HATU and 9 equivalents of NMM in NMP and pyridine (2:1).

Step 7: Reaction of the activated protected compound of the general formula II, or of a correspondingly protected amino acid, respectively, with the solid phase (1. coupling; time period: 30 min).

Step 8: 4× Washing with NMP.

Step 9: 1× Washing with dichloromethane.

Step 10: Repetition of steps 6 to 8 (2. coupling).

Step 11: Examination of the efficiency of the coupling with ninhydrin (Kaiser's test; if the Kaiser's test shows a positive result, the steps 6 to 8 have to be repeated with the corresponding protected compound of the general formula II).

Step 12: After a negative Kaiser's test, the reaction sequence is capped twice with a solution of $Ac_2O$, NMP, and pyridine (1:15:25) for 4 min each.

Step 13: 5× Washing with NMP.

Step 14: Repeating of the synthesis cycles (steps 2 to 13) up to the coupling of the linker eg1 (8-amino-2,6-dioxa octanoic acid)

Step 15: Coupling of the linkers: 4× Washing with dichloromethane

Step 16: Cleavage of the Boc group by reaction with TFA and m-cresol (95:5). Reaction period: 2×3 min in each case.

Step 17: 5× Washing with dichloromethane.

Step 18: 5× Washing with NMP.

Step 19: 1 min Preactivation of 4 equivalents of eg1 with 3.8 equivalents of HATU and 9 equivalents of NMM in NMP and pyridine (2:1).

Step 20: Reaction of the activated linker with the solid phase (1. coupling; time period: 30 min).

Step 21: 4× Washing with NMP.

Step 22: 1× Washing with dichloromethane.

Step 23: Repetition of steps 19 to 21 (2. coupling).

Step 24: Examination of the efficiency of the coupling with ninhydrin (Kaiser's test; if the Kaiser's test shows a positive result, the steps 19 to 21 have to be repeated).

Step 25: 2× Capping with a solution of $Ac_2O$, NMP, and pyridine (1:15:25) for 4 min each after a negative Kaiser's test.

Step 26: 5× Washing with NMP.

Step 27: 2× Repeating of the synthesis steps (steps 15 to 26) for $(eg1)_3$.

Step 28: Repeating of the synthesis cycles (steps 2 to 13) up to the coupling with the final corresponding protected compound of the general formula II. Subsequently, the synthesis cycles are optionally repeated (steps 2 to 13) up to the coupling with the final correspondingly protected amino acid.

Step 29: After the coupling of the final corresponding protected compound of the general formula II, or of a correspondingly protected amino acid, respectively, the steps 2 to 5 for the final cleavage of the Boc group and the steps 12 and 13 (without a preceding Kaiser's test) are performed for final capping.

Step 30: 5× Washing with dichloromethane.

Step 31: For drying: 5× washing with diethyl ether.

A compound of the general formula I is obtained that is bound to the resin at the carboxylic acid terminal end.

Cleavage of the compound according to the invention from the resin:

The resin with the compound according to the invention is stirred in an aqueous ammonia solution (28-30 weight percent $NH_3$ in $H_2O$) at 60° C. for 20 h. The cleaved resin then will be separated by filtration, and the filtrate is concentrated in vacuo and dried. The crude product is purified by preparative HPLC via a RP-C18 column with methanol and water. The compound according to the invention having a linker is obtained as a colorless solid in a yield of 50%. The molecular weight of the compound according to the invention having a linker is characterized by MALDI-TOF.

Example 13: Further Examples of Sequences

Further compounds according to the invention are produced by carrying out the general synthesis specifications of examples 11 or 12:

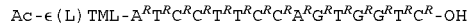

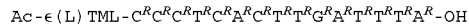

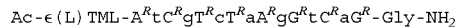

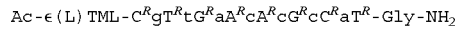

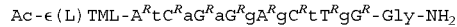

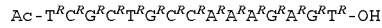

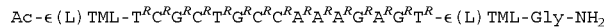

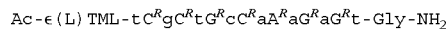

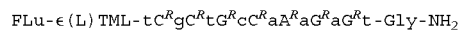

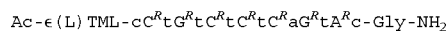

Ac-ε(L)TML-G$^R$tC$^R$tC$^R$tC$^R$aG$^R$tA$^R$cA$^R$aT$^R$-Gly-NH$_2$

Ac-ε(L)TML-G$^R$C$^R$T$^R$C$^R$C$^R$T$^R$C$^R$G$^R$C$^R$C$^R$T$^R$T$^R$G$^R$C$^R$-ε(L)TML-Gly-NH$_2$

Ac-ε(L)TML-G$^R$C$^R$T$^R$C$^R$C$^R$T$^R$C$^R$G$^R$C$^R$C$^R$T$^R$T$^R$G$^R$C$^R$-ε(L)TML-Gly-NH$_2$

Ac-ε(L)TML-A$^R$G$^R$C$^R$T$^R$C$^R$C$^R$T$^R$C$^R$G$^R$C$^R$C$^R$T$^R$T$^R$G$^R$C$^R$-Gly-NH$_2$

Ac-ε(L)TML-ε(L)TML-ε(L)TML-ε(L)TML-tC$^R$aC$^R$cA$^R$tG$^R$gT$^R$gG$^R$cG$^R$aC$^R$-Gly-NH$_2$

Ac-ε(L)TML-ε(L)TML-ε(L)TML-ε(L)TML-aG$^R$cT$^R$cC$^R$tC$^R$gC$^R$cC$^R$tT$^R$gC$^R$-Gly-NH$_2$

Ac-ϵ(L)TML-ϵ(L)TML-ϵ(L)TML-ϵ(L)TML-tG$^R$gT$^R$cG$^R$gG$^R$gT$^R$aG$^R$cG$^R$gC$^R$-Gly-NH$_2$

Ac-ϵ(L)TML-ϵ(L)TML-ϵ(L)TML-ϵ(L)TML-cT$^R$gC$^R$aC$^R$gC$^R$tG$^R$cC$^R$gT$^R$cC$^R$-Gly-NH$_2$

Ac-ϵ(L)TML-ϵ(L)TML-ϵ(L)TML-ϵ(L)TML-gT$^R$tC$^R$tG$^R$cT$^R$gG$^R$tA$^R$gT$^R$gG$^R$-Gly-NH$_2$

Ac-ϵ(L)TML-C$^R$T$^R$T$^R$C$^R$G$^R$C$^R$A$^R$C$^R$T$^R$C$^R$A$^R$-ϵ(L)TML-Gly-NH$_2$

Ac-cT$^R$tC$^R$gC$^R$aC$^R$tC$^R$a-ϵ(L)TML-Gly-NH$_2$

Ac-ϵ(L)TML-cT$^R$tC$^R$gC$^R$aC$^R$tC$^R$a-eg1-eg1-eg1-Gly-NH$_2$

Ac-ϵ(L)TML-ϵ(L)TML-ϵ(L)TML-ϵ(L)TML-cT$^R$tC$^R$gC$^R$aC$^R$tC$^R$a-eg1-eg1-eg1-tJ$^S$tJ$^S$-Gly-NH$_2$

Ac-ϵ(L)TML-ϵ(L)TML-ϵ(L)TML-ϵ(L)TML-cT$^R$tC$^R$gC$^R$aC$^R$tC$^R$a-eg1-eg1-eg1-tJ$^R$tJ$^R$-Gly-NH$_2$

Ac-G$^R$C$^R$T$^R$G$^R$C$^R$C$^R$A$^R$A$^R$A$^R$G$^R$A$^R$G$^R$T$^R$-Gly-NH$_2$

Ac-ϵ(L)TML-tcgcT$^R$G$^R$C$^R$C$^R$A$^R$A$^R$A$^R$gagt-Gly-NH$_2$

Ac-ϵ(L)TML-ϵ(L)TML-ϵ(L)TML-ϵ(L)TML-T$^R$C$^R$G$^R$ctgccaaagA$^R$G$^R$T$^R$-ϵ(L)TML-Gly-NH$_2$ Ac-ϵ(L)TML-tcgctgccaaagA$^R$G$^R$T$^R$-ϵ(L)TML-Gly-NH$_2$ Ac-ϵ(L)TML-T$^R$C$^R$G$^R$ctgccaaagagt-ϵ(L)TML-Gly-NH$_2$ Ac-ϵ(L)TML-ϵ(L)TML-ϵ(L)TML-T$^R$C$^R$gctgC$^R$C$^R$aaagaG$^R$T$^R$-Gly-NH$_2$ Ac-ϵ(L)TML-T$^R$cgC$^R$tgC$^R$caA$^R$agA$^R$gt-Gly-NH$_2$ Ac-ϵ(L)TML-ϵ(L)TML-T$^R$cgctgcC$^R$aaagag$^R$T$^R$-Gly-NH$_2$ Ac-ϵ(L)TML-tcgctgC$^R$C$^R$aaagagt-Gly-NH$_2$ Ac-ϵ(L)TML-tcgcT$^R$gccaaA$^R$gagt-Gly-NH$_2$ Ac-ϵ(L)TML-T$^R$cgctgccaaagagT$^R$-Gly-NH$_2$ Ac-ϵ(L)TML-tcgctgccaaagagT$^R$-Gly-NH$_2$ Ac-ϵ(L)TML-T$^R$cgctgccaaagagt-Gly-NH$_2$ Ac-ϵ(L)TML-tcgctgccA$^R$aagagt-Gly-NH$_2$ Ac-ϵ(L)TML-gG$^R$cT$^R$cC$^R$cA$^R$aA$^R$gA$^R$tC$^R$tT$^R$-Gly-NH$_2$ Ac-ϵ(L)TML-T$^R$cG$^R$gA$^R$gC$^R$cA$^R$gC$^R$cC$^R$cT$^R$t-Gly-NH$_2$ Ac-ϵ(L)TML-G$^R$tA$^R$tT$^R$cA$^R$gT$^R$gT$^R$gA$^R$tG$^R$a-Gly-NH$_2$ Ac-ϵ(L)TML-gC$^R$tA$^R$tT$^R$aC$^R$cT$^R$tA$^R$aC$^R$cC$^R$-Gly-NH$_2$ Ac-ϵ(L)TML-gC$^R$aA$^R$aT$^R$tC$^R$tT$^R$aT$^R$tC$^R$cC$^R$-Gly-NH$_2$ Ac-ϵ(L)TML-A$^R$aA$^R$tC$^R$aG$^R$gG$^R$tT$^R$aG$^R$gT$^R$-Gly-NH$_2$ Flu-ϵ(L)TML-A$^R$aA$^R$tC$^R$aG$^R$gG$^R$tT$^R$aG$^R$gT$^R$-Gly-NH$_2$ Ac-ϵ(L)TML-cG$^R$cC$^R$tT$^R$aT$^R$cC$^R$gT$^R$aG$^R$cC$^R$-Gly-NH$_2$ Flu-ϵ(L)TML-cG$^R$cC$^R$tT$^R$aT$^R$cC$^R$gT$^R$aG$^R$cC$^R$-Gly-NH$_2$ Ac-ϵ(L)TML-C$^R$gT$^R$gT$^R$cT$^R$gT$^R$gT$^R$tG$^R$tA$^R$g-Gly-NH$_2$ Ac-ϵ(L)TML-cA$^R$cG$^R$tA$^R$tG$^R$cT$^R$tC$^R$gT$^R$cT$^R$-Gly-NH$_2$ Ac-(ϵ(L)TML)$_4$-tA$^R$tT$^R$aC$^R$tT$^R$cT$^R$gG$^R$gC$^R$tG$^R$-Gly-NH$_2$ LiRho-(ϵ(L)TML)$_4$-tA$^R$tT$^R$aC$^R$tT$^R$cT$^R$gG$^R$gC$^R$tG$^R$-Gly-NH$_2$ -continued

LiRho = Lissamine Rhodanin B (Sulforhodamine B)

Ac-(ε(L)TML)$_4$-cT$^R$cT$^R$tG$^R$aT$^R$aA$^R$aT$^R$tT$^R$gA$^R$-Gly-NH$_2$

LiRho-(ε(L)TML)$_4$-cT$^R$cT$^R$tG$^R$aT$^R$aA$^R$aT$^R$tT$^R$gA$^R$-Gly-NH$_2$

Ac-(ε(L)TML)$_4$-tG$^R$gT$^R$gA$^R$aA$^R$tT$^R$gC$^R$tG$^R$cC$^R$-Gly-NH$_2$

LiRho-(ε(L)TML)$_4$-tG$^R$gT$^R$gA$^R$aA$^R$tT$^R$gC$^R$tG$^R$cC$^R$-Gly-NH$_2$

Ac-(ε(L)TML)$_4$-gA$^R$gC$^R$tC$^R$tT$^R$cG$^R$tC$^R$gC$^R$tG$^R$-Gly-NH$_2$

LiRho-(ε(L)TML)$_4$-gA$^R$gC$^R$tC$^R$tT$^R$cG$^R$tC$^R$gC$^R$tG$^R$-Gly-NH$_2$

Ac-(ε(L)TML)$_4$-cT$^R$cC$^R$aT$^R$tA$^R$tC$^R$aT$^R$tC$^R$tC$^R$-Gly-NH$_2$

LiRho-(ε(L)TML)$_4$-cT$^R$cC$^R$aT$^R$tA$^R$tC$^R$aT$^R$tC$^R$tC$^R$-Gly-NH$_2$

Ac-(ε(L)TML)$_4$-cC$^R$cT$^R$gG$^R$tG$^R$tG$^R$tA$^R$gT$^R$tC$^R$-Gly-NH$_2$

LiRho-(ε(L)TML)$_4$-cC$^R$cT$^R$gG$^R$tG$^R$tG$^R$tA$^R$gT$^R$tC$^R$-Gly-NH$_2$

Ac-(ε(L)TML)$_4$-A$^R$gC$^R$tcctcG$^R$cC$^R$cT$^R$tG$^R$c-Gly-NH$_2$

TxRed-(ε(L)TML)$_4$-A$^R$gC$^R$tcctcG$^R$cC$^R$cT$^R$tG$^R$c-Gly-NH$_2$
TxRed = Texas Red (Sulforhodamine 101)

Ac-(ε(L)TML)$_4$-A$^R$gC$^R$tC$^R$cT$^R$cG$^R$cC$^R$cT$^R$tgc-Gly-NH$_2$

TxRed-(ε(L)TML)$_4$-A$^R$gC$^R$tC$^R$cT$^R$cG$^R$cC$^R$cT$^R$tgc-Gly-NH$_2$

Ac-((L)Lys))$_4$-G$^R$tA$^R$tT$^R$cA$^R$gtgtgA$^R$tG$^R$a-Gly-NH$_2$

Ac-(ε(L)TML)$_4$-G$^R$tA$^R$tT$^R$cA$^R$gtgtgA$^R$tG$^R$a-Gly-NH$_2$

Ac-(ε(L)TML)$_4$-gtatT$^R$cA$^R$gtgtgA$^R$tG$^R$a-Gly-NH$_2$

Ac-(ε(L)TML)$_4$-cG$^R$cC$^R$tT$^R$atccgT$^R$aG$^R$cC$^R$-Gly-NH$_2$

Ac-(L-Lys)$_4$-gC$^R$tA$^R$tT$^R$cccttA$^R$aC$^R$cC$^R$-Gly-NH$_2$

TxRed-(L-Lys)$_4$-gC$^R$tA$^R$tT$^R$accttA$^R$aC$^R$cC$^R$-Gly-NH$_2$

Ac-(L-Lys)-(L-Lys)-(L-Lys)-(L-Arg)-(L-Lys)-(L-Val)-gC$^R$tA$^R$tT$^R$accttA$^R$aC$^R$cC$^R$-Gly-NH$_2$ TxRed-(L-Lys)-(L-Lys)-(L-Lys)-(L-Arg)-(L-Lys)-(L-Val)-gC$^R$tA$^R$tT$^R$accttA$^R$aC$^R$cC$^R$-Gly-NH$_2$ Ac-(ε(L)TML)$_4$-gC$^R$tA$^R$tT$^R$accttA$^R$aC$^R$cC$^R$-Gly-NH$_2$ TxRed-(ε(L)TML)$_4$-gC$^R$tA$^R$tT$^R$accttA$^R$aC$^R$cC$^R$-Gly-NH$_2$ Ac-(ε(L)TML)$_4$-acttG$^R$aA$^R$ttcgtA$^R$tCRc-Gly-NH$_2$ Ac-(L-Lys)-(L-Lys)-(L-Lys)-(L-Arg)-(L-Lys)-(L-Val)-acttG$^R$aA$^R$ttcgtA$^R$tC$^R$c-Gly-NH$_2$ Ac-(ε(L)TML)$_4$-acttG$^R$aattcgtA$^R$tC$^R$c-Gly-NH$_2$ Ac-(L-Lys)-(L-Lys)-(L-Lys)-(L-Arg)-(L-Lys)-(L-Val)-acttG$^R$aattcgtA$^R$tC$^R$c-Gly-NH$_2$ AC-(ε(L)TML)$_4$-gtgtA$^R$TA$^R$cacggA$^R$aT$^R$a-Gly-NH$_2$ Flu-(ε(L)TML)$_4$-gtgtA$^R$tA$^R$cacggA$^R$aT$^R$a-Gly-NH$_2$ Ac-(L-Lys)-(L-Lys)-(L-Lys)-(L-Arg)-(L-Lys)-(L-Val)-gtgtA$^R$tA$^R$cacggA$^R$aT$^R$a-Gly-NH$_2$ Flu-(L-Lys)-(L-Lys)-(L-Lys)-(L-Arg)-(L-Lys)-(L-Val)-gtgtA$^R$tA$^R$cacggA$^R$aT$^R$a-Gly-NH$_2$ Ac-(ε(L)TML)$_4$-gtgtA$^R$tacacggA$^R$aT$^R$a-Gly-NH$_2$ Flu-(ε(L)TML)$_4$-gtgtA$^R$tacacggA$^R$aT$^R$a-Gly-NH$_2$ Ac-(ε(L)TML)$_4$-ctgcT$^R$gC$^R$tgctgC$^R$tG$^R$c-Gly-NH$_2$ Ac-(L-Lys)-(L-Lys)-(L-Lys)-(L-Arg)-(L-Lys)-(L-Val)-ctgcT$^R$gC$^R$tgctgC$^R$tG$^R$c-Gly-NH$_2$ Ac-(ε(L)TML)$_4$-ctgcT$^R$gctgctgC$^R$tG$^R$c-Gly-NH$_2$ Ac-(L-Lys)-(L-Lys)-(L-Lys)-(L-Arg)-(L-Lys)-(L-Val)-ctgcT$^R$gctgctgC$^R$tG$^R$c-Gly-NH$_2$ Ac-(ε(L)TML)$_4$-agctC$^R$cT$^R$cggtaG$^R$gT$^R$c-Gly-NH$_2$ -continued Ac-(L-Lys)-(L-Lys)-(L-Lys)-(L-Arg)-(L-Lys)-(L-Val)-agctC$^R$cT$^R$cggtaG$^R$gT$^R$c-Gly-NH$_2$ Ac-(ε(L)TML)$_4$-agctC$^R$ctcggtaG$^R$gT$^R$c-Gly-NH$_2$ Ac-(L-Lys)-(L-Lys)-(L-Lys)-(L-Arg)-(L-Lys)-(L-Val)-agctC$^R$ctcggtaG$^R$gT$^R$c-Gly-NH$_2$ Ac-gtccC$^R$tG$^R$aagatG$^R$tC$^R$a-Gly-NH$_2$ Ac-(ε(L)TML)$_4$-gtccC$^R$tG$^R$aagatG$^R$tC$^R$a-Gly-NH$_2$ Ac-gtatT$^R$cA$^R$gtgtgA$^R$tG$^R$a-Gly-NH$_2$ Ac-(ε(L)TML)$_4$-gtatT$^R$cA$^R$gtgtgA$^R$tG$^R$a-Gly-NH$_2$ Ac-gtcgC$^R$tG$^R$tctccG$^R$cT$^R$t-Gly-NH$_2$ Ac-(ε(L)TML)$_4$-gtcgC$^R$tG$^R$tctccG$^R$cT$^R$t-Gly-NH$_2$ Ac-(ε(L)TML)$_4$-ctccA$^R$tG$^R$gtgctC$^R$aC$^R$t-Gly-NH$_2$ Ac-(DEPABS)$_2$-Gly-ctccA$^R$tG$^R$gtgctC$^R$aC$^R$t-Gly-NH$_2$ Ac-(ε(L)TML)$_4$-ggctC$^R$cC$^R$aaagaT$^R$cT$^R$t-Gly-NH$_2$ Ac-(DEPABS)$_2$-Gly-ggctC$^R$cC$^R$aaagaT$^R$cT$^R$t-Gly-NH$_2$ Ac-(ε(L)TML)$_4$-tcggA$^R$gC$^R$cagccC$^R$cT$^R$t-Gly-NH$_2$ Ac-(DEPABS)$_2$-Gly-tcggA$^R$gC$^R$cagccC$^R$cT$^R$t-Gly-NH$_2$ Ac-(ε(L)TML)$_4$-tcccA$^R$gC$^R$gtgcgC$^R$cA$^R$t-Gly-NH$_2$ Ac-(DEPABS)$_2$-Gly-tcccA$^R$gC$^R$gtgcgC$^R$cA$^R$t-Gly-NH$_2$ Ac-(ε(L)TML)$_4$-catcC$^R$cA$^R$gcctcC$^R$gT$^R$t-Gly-NH$_2$ Ac-(DEPABS)$_2$-Gly-catcC$^R$cA$^R$gcctcC$^R$gT$^R$t-Gly-NH$_2$ Ac-(ε(L)TML)$_4$-gtcgC$^R$tG$^R$tctccG$^R$cT$^R$t-Gly-NH$_2$ Ac-(DEPABS)$_2$-Gly-gtcgC$^R$tG$^R$tctccG$^R$cT$^R$t-Gly-NH$_2$ Ac-(L-Lys)-(L-Lys)-(L-Lys)-(L-Arg)-(L-Lys)-(L-Val)-gtcgC$^R$tG$^R$tctccG$^R$cT$^R$t-Gly-NH$_2$ Ac-(L-Lys)-(L-Lys)-(L-Lys)-(L-Arg)-(L-Lys)-(L-Val)-ctgcT$^R$gC$^R$tgctgC$^R$tG$^R$c-Gly-NH$_2$ Ac-(DEPABS)$_2$-Gly-ctgcT$^R$gC$^R$tggctgC$^R$tG$^R$c-Gly-NH$_2$ Ac-L-Lys)-(L-Lys)-(L-Lys)-(L-Arg)-(L-Lys)-(L-Val)-agctC$^R$cT$^R$cgcccT$^R$tG$^R$c-Gly-NH$_2$ Ac-(DEPABS)$_2$-Gly-agctC$^R$cT$^R$cgcccT$^R$tG$^R$c-Gly-NH$_2$ Ac-(L-Lys)-(L-Lys)-(L-Lys)-(L-Arg)-(L-Lys)-(L-Val)-gcgtG$^R$tG$^R$ggaagG$^R$cA$^R$g-Gly-NH$_2$ Ac-(DEPABS)$_2$-Gly-gcgtG$^R$tG$^R$ggaagG$^R$cA$^R$g-Gly-NH$_2$ DOTA-$\epsilon$(L)TML-C$^R$aG$^R$tT$^R$aG$^R$gG$^R$tT$^R$aG$^R$-Gly-NH$_2$

Example 14: Stronger Antisense Effect of Compounds According to the Invention Compared with Stereochemically Non-Uniform Oligomers H9 cells, chronically infected with strain HIV-1-NL4-3 are washed twice with a PBS buffer in order to remove viruses already produced. The cells are incubated in a 96-well plate with 104 cells/well, 4 wells per sample, in 200 μl culturing medium with or without a compound according to the invention or Ritonavir, respectively, at a distinct concentration. After 5 days of incubation, 40 μl of the cell suspension are taken from each of the 4 wells and inactivated with 40 μl Nonidet P-40.

The amount of the antigen p24 GAG is determined by a quantitative ELISA assay (Sandwich-ELISA-Biotin-Strepavidin-HRP) according to the standard method of the Institute for Applied Microbiology in Vienna. As a standard, samples with a known amount of p24 are used to investigate the standard calibration curve.

In this context, in the case of stereochemically non-uniform oligomers of the sequence TCGCTGC-CAAAGAGT-NH$_2$ (SEQ ID NO: 1), a reduction of the amount of p24 of 21% can be observed compared with the untreated sample. The shorter compounds according to the invention having the sequence T$^R$A$^R$G$^R$A$^R$G$^R$C$^R$-T$^R$T$^R$C$^R$C$^R$—NH$_2$ showed an increased reduction of 36%.

Example 15: Effectiveness Against HIV Over Two Daughter Generations

Human CD4$^+$ T-lymphocytes (M8166) were preincubated with the compounds according to the invention for 24 hours, and subsequently infected with HIV (primary infection).

After 6 days, the supernatant with the new formed HI viruses is separated from the cells by centrifugation. The supernatant is diluted as necessary in order to obtain a HIV proliferation during the subsequent infection (secondary infection) in a range that could be measured according to the standard method (ca. 1:5.000). Subsequently, non-infected cells (M8166) were infected with HIV from the diluted supernatant, and the amount of p24 is measured by means of a quantitative p24 ELISA test after further 6 days.

In the experiment, the compounds according to the invention having an effective HIV sequence (match) which can bind to HIV RNA due to their sequence, are used. Furthermore, the compounds according to the invention are used whose sequence does not exhibit a match for a binding to HIV RNA (no-match). The obtained measurements from the quantitative p24 ELISA test after the secondary infection were correlated with the obtained measurements from the positive control for which no compounds according to the invention were used, and the results are summarized in the following table.

| no compounds according to the invention (positive control) | | | | | |
|---|---|---|---|---|---|
| P24 [%] | | | 100 | | |
| compounds according to the invention (match): | | | | | |
| Ac-ε(L)TML-T$^R$C$^R$G$^R$C$^R$T$^R$G$^R$C$^R$C$^R$A$^R$A$^R$A$^R$G$^R$A$^R$G$^R$T$^R$-ε(L)TML-Gly-NH$_2$ | | | | | |
| concentration [μM] | 25 | 12.5 | 6.25 | 3.125 | 1.5625 |
| P24 [%] | 18 | 20 | 73 | 48 | 68 |
| compounds according to the invention (no-match): | | | | | |
| Ac-ε(L)TML-G$^R$C$^R$T$^R$C$^R$C$^R$T$^R$C$^R$G$^R$C$^R$C$^R$C$^R$T$^R$T$^R$G$^R$C$^R$-ε(L)TML-Gly-NH$_2$ | | | | | |
| concentration [μM] | 25 | 12.5 | 6.25 | 3.125 | 1.5625 |
| P24 [%] | 64 | 84 | 84 | 71 | 90 |

After the second infection, however, a clear reduction of the p24 concentration can be detected for the compounds according to the invention having a HIV sequence at the two highest used concentrations.

Example 16: Accumulation of Compounds According to the Invention in Cells Having a Target Sequence The compounds according to the invention accumulate surprisingly strong in cells that have a complementary DNA or RNA sequence, respectively.

In a corresponding experiment, compounds according to the invention having a HIV sequence which compounds are able to bind to a complementary DNA or RNA sequence, respectively, have been labeled with fluorescein (Flu). Once HIV infected human CD4$^+$ T-lymphocytes (M8166) and non-infected human CD4$^+$ T-lymphocytes (M8166) are incubated with these labeled compounds according to the invention.

The FACS analysis of the respective cells exhibits a significantly higher accumulation of the compounds according to the invention having a HIV sequence in the HIV-infected cells, where a complementary DNA or RNA sequence, respectively, is present.

Figure 2:
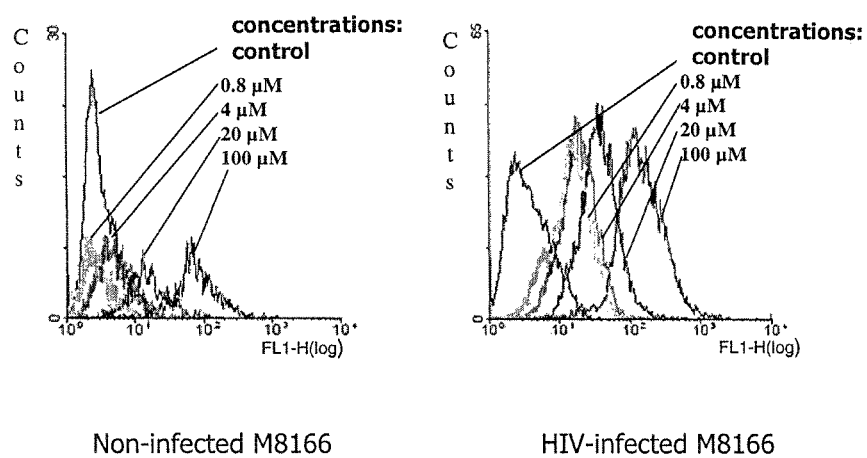
FIG. 2 shows the results of FACS analysis of non-infected human CD4$^+$ T-lymphocytes (left) and HIV-infected human CD4$^+$ T-lymphocytes (right) incubated with compound Flu-ϵTML-T$^R$C$^R$G$^R$C$^R$T$^R$G$^R$C$^R$C$^R$A$^R$A$^R$A$^R$G$^R$A$^R$G$^R$T$^R$-Gly-NH$_2$.

In FIG. 2, the corresponding results are presented using the compound according to the invention Flu-εTML-T$^R$C$^R$-G$^R$C$^R$T$^R$G$^R$C$^R$C$^R$A$^R$A$^R$A$^R$G$^R$A$^R$G$^R$T$^R$-Gly-NH$_2$.

Example 17: Comparison of Cell Permeability of Different Compounds According to the Invention Using the same experimental setup as in example 16, the cell permeability of compounds according to the invention having a substituting rest R$^1$ at each asymmetric center is compared with the cell permeability of compounds according to the invention at which the rest R$^1$ is replaced by a hydrogen atom at each second asymmetric center.

The FACS analyses of the respective cells exhibit no difference in the cell permeability between the two groups of compounds according to the invention.

Figure 3:
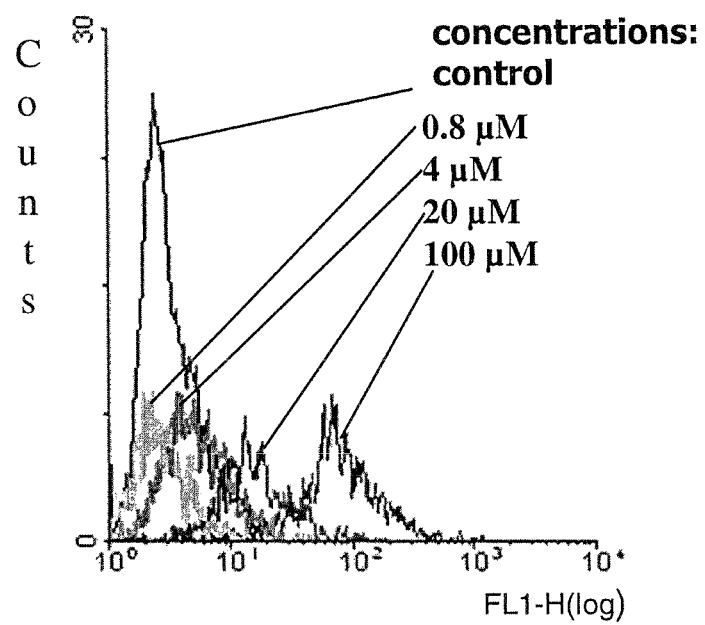
FIG. 3 shows the results of FACS analysis of human CD4$^+$ T-lymphocytes incubated with compound Flu-ϵTML-T$^R$C$^R$G$^R$C$^R$T$^R$G$^R$C$^R$C$^R$A$^R$A$^R$A$^R$G$^R$A$^R$G$^R$T$^R$-Gly-NH$_2$.

In FIG. 3 the corresponding results are presented using the compound according to the invention Flu-εTML-T$^R$C$^R$G$^R$-C$^R$T$^R$G$^R$C$^R$C$^R$A$^R$A$^R$A$^R$G$^R$A$^R$G$^R$T$^R$-Gly-NH$_2$.

Figure 4:
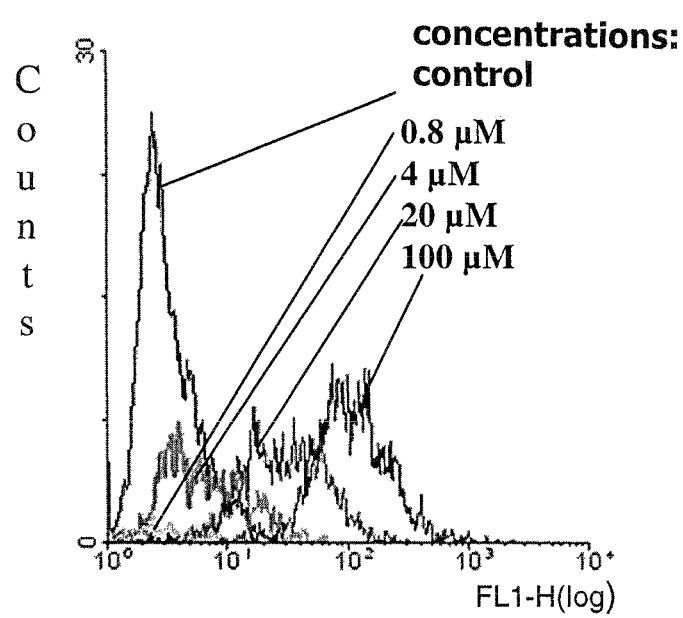
FIG. 4 shows the results of FACS analysis of human CD4$^+$ T-lymphocytes incubated with compound Flu-ϵTML-tC$^R$gC$^R$tG$^R$cC$^R$aA$^R$aG$^R$aG$^R$t-Gly-NH$_2$.

In FIG. 4 the corresponding results are presented using the compound according to the invention Flu-εTML-tC$^R$gC$^R$t-G$^R$cC$^R$aA$^R$aG$^R$aG$^R$t-Gly-NH$_2$.

Example 18: Detection of Compounds According to the Invention in the Tissue of the Gastrointestinal Tract and the Air Bladder of Medaka Fishes Medaka fishes were kept for two days in a 100 μM solution of the compound according to the invention TxRed-(εTML)-4-A$^R$GC$^R$TC$^R$CT$^R$CG$^R$CC$^R$CT$^R$TGC-Gly-NH$_2$, and then, they are transferred into fresh water. Subsequently, the distribution of the compound according to the invention within the fishes at day one, as well as at days 2 and 5 after the transfer into fresh water is investigated under the fluorescence microscope. The pictures show that even after 5 days the compounds according to the invention can be detected in the gastrointestinal tract.

FIG. 5 shows the corresponding fluorescence microscopic photographs.

Example 19: In Vivo Reduction of Cholesterol, ApoB100 and ApoB48 in Mice by Intravenous Treatment with Compounds According to the Invention The compound according to the invention Ac-(εTML)-4-gtatT$^R$cA$^R$gtgtgA$^R$tG$^R$a-Gly-NH$_2$, representing a matching sequence to the target sequence of ApoB100, was investigated in respect of its pharmacological effectiveness in mice. As a negative control, the injection of pure PBS buffer was used. In this context, the mice were administered three different concentrations (25 mg/kg, 12.5 mg/kg, 6.25 mg/kg) of an effective compound according to the invention (solved in PBS buffer) or of the control buffer in portions of 0.1 ml intravenously once daily at three subsequent days. At the fourth day, blood samples were taken from the mice and investigated in respect of their content of cholesterol, ApoB100 and ApoB48. The values of the following table show the concentrations of cholesterol and ApoB100 in relation to the mice treated only with PBS.

| Compound according to the invention: Ac-(εTML)$_4$-gtatT$^R$cA$^R$gtgtgA$^R$tG$^R$a-Gly-NH$_2$ | | | |
|---|---|---|---|
| concentration [mg/kg] | 25 | 12.5 | 6.25 |
| Cholesterol [%] | 75 | 85 | 98 |
| ApoB 100 [%] | 59 | 67 | — |
| ApoB 48 [%] | 68 | 74 | 80 |

The results demonstrate a clear and concentration dependent reduction of cholesterol, ApoB100 and ApoB48 in the blood of the mice.

Example 20: Effectiveness of the Compounds According to the Invention Against Cancer The compound according to the invention Ac-εTML-T$^R$cG$^R$gA$^R$gC$^R$cA$^R$gC$^R$cC$^R$cT$^R$T$^R$t-Gly-NH$_2$, representing a matching sequence to the target sequence of Her2/neu was investigated in respect of its proliferation inhibiting action of the cell line MDA453 overexpressing Her2/neu. As a negative control, the compound according to the invention Ac-εTML-cG$^R$cC$^R$tT$^R$aT$^R$cC$^R$gT$^R$aG$^R$cC$^R$-Gly-NH$_2$ was used which does not represent a matching sequence to the target sequence of Her2/neu, as well as untreated MDA453 control cells.

At the first day, between 5.000 and 10.000 MDA453 cells were seeded into 96 well plates. At the second day, the matching sequence according to the invention, or the control sequence according to the invention, respectively, are each added in a concentration of 1 μM. At the days 3, 4 and 5, the cell medium is changed and replaced by fresh medium containing the compounds according to the invention in a concentration of 1 μM, respectively. The proliferation inhibiting action is specified by the determination of the DNA content in the individual wells by means of propidium iodide.

| no compound according to the invention (negativ control) |
|---|
| DNA [%] 100 |
| compound according to the invention (match): Ac-εTML-T$^R$cG$^R$gA$^R$gC$^R$cA$^R$gC$^R$cC$^R$cT$^R$t-Gly-NH$_2$ |
| DNA [%] 67 |
| compound according to the invention (no-match): Ac-εTML-cG$^R$cC$^R$tT$^R$aT$^R$cC$^R$gT$^R$aG$^R$cC$^R$-Gly-NH$_2$ |
| DNA [%] 103 |

The invention claimed is:
1. Compound of the formula I,

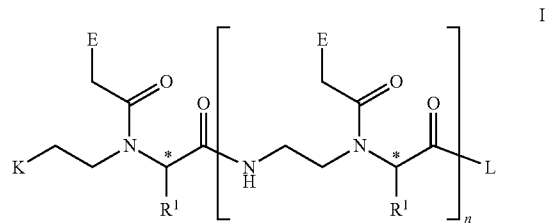

wherein
n represents an integer from 7 to 35,
each E independently of each other represents a substituted or unsubstituted phenyl group, a substituted or unsubstituted heterocycle, or a nucleobase,
each R$^1$ independently of each other represents a hydrogen atom or an optionally substituted alkyl, alkenyl, alkylaryl, aryl, heterocyclic or alicyclic group having up to 20 carbon atoms, wherein at least one R$^1$ is an optionally substituted alkyl, alkenyl, alkylaryl, aryl, heterocyclic or alicyclic group having up to 20 carbon atoms which is substituted with one or more phosphonic acid ester functions or phosphonic acid functions, wherein the phosphonic acid ester functions possess the formula —P(=O)(OV)$_2$ or —P(=O)(OV)(OH), wherein each V independently of each other represents a methyl, ethyl, cyclohexyl or benzyl group,
K represents a group of the formula —NR$^2$R$^3$, —N$^⊕$R$^2$R$^3$R$^4$, or —NR$^2$(CO)R$^3$, wherein R$^2$, R$^3$ and R$^4$ independently of each other represent a hydrogen atom, an alkyl group, amino protecting group, fluorescence marker, chelator, amino acid, peptide, carbohydrate, steroid, fatty acid, or an oligonucleotide, wherein each of the above mentioned groups optionally may be substituted,
L represents a group of the formula —NR$^5$R$^6$, —NR$^5$(CO)R$^6$, or —OR$^7$, wherein R$^5$ and R$^6$ independently of each other represent a hydrogen atom, an alkyl group, fluorescence marker, chelator, amino acid, amino acid amide, peptide, peptide amide, carbohydrate, steroid, fatty acid, or an oligonucleotide, wherein each of the above mentioned groups optionally may be substituted, and wherein R$^7$ represents a hydrogen atom, an alkyl group, fluorescence marker, chelator, amino acid, peptide, peptide amide, carbohydrate, ste-

SEQUENCE LISTING

<160> NUMBER OF SEQ ID NOS: 1

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: 3'-NH2

<400> SEQUENCE: 1
tcgctgccaa agagt                                                    15 roid, fatty acid, or an oligonucleotide, wherein each of the above mentioned groups optionally may be substituted, wherein the compound of the formula I has 2 to 36 asymmetric centers (*) and 1 to 36 optionally substituted groups $R^1$ having one or more phosphonic acid ester function(s) or phosphonic acid function(s), and wherein at least 70% of the number of the asymmetric centers (*) having groups $R^1$ with one or more phosphonic acid ester function(s) or phosphonic acid function(s) exhibit the R configuration or the S configuration, and at most 40% of the number of the groups $R^1$ being substituted with phosphonic acid ester functions or phosphonic acid functions.

2. Compound according to claim 1, wherein each second group $R^1$ or each third group $R^1$ independently of each other represents an optionally substituted alkyl, alkenyl, alkylaryl, aryl or alicyclic group having up to 20 carbon atoms, and the remaining groups $R^1$ represent hydrogen atoms.

3. Compound of formula I,

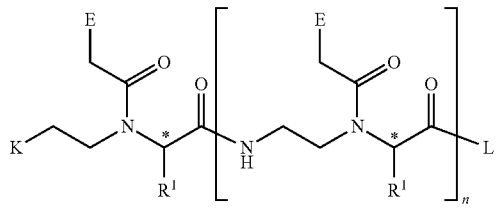

wherein n represents an integer from 7 to 35, each E independently of each other represents a substituted or unsubstituted phenyl group, a substituted or unsubstituted heterocycle, or a nucleobase, two, three or more adjacent $R^1$ groups independently of each other represent optionally substituted alkyl, alkenyl, alkylaryl, aryl or alicyclic groups having up to 20 carbon atoms, and the remaining $R^1$ groups represent hydrogen atoms, K represents a group of the formula —$NR^2R^3$, —$N^{\oplus}R^2R^3R^4$, or —$NR^2(CO)R^3$, wherein $R^2$, $R^3$ and $R^4$ independently of each other represent a hydrogen atom, an alkyl group, amino protecting group, fluorescence marker, chelator, amino acid, peptide, carbohydrate, steroid, fatty acid, or an oligonucleotide, wherein each of the above mentioned groups optionally may be substituted, L represents a group of the formula —$NR^5R^6$, —$NR^5(CO)R^6$, or —$OR^7$, wherein $R^5$ and $R^6$ independently of each other represent a hydrogen atom, an alkyl group, fluorescence marker, chelator, amino acid, amino acid amide, peptide, peptide amide, carbohydrate, steroid, fatty acid, or an oligonucleotide, wherein each of the above mentioned groups optionally may be substituted, and wherein $R^7$ represents a hydrogen atom, an alkyl group, fluorescence marker, chelator, amino acid, peptide, peptide amide, carbohydrate, steroid, fatty acid, or an oligonucleotide, wherein each of the above mentioned groups optionally may be substituted, wherein the compound of the formula I has 2 to 36 asymmetric centers (*) and 1 to 36 optionally substituted $R^1$ groups having one or more phosphonic acid ester function(s) or phosphonic acid function(s), and wherein at least 70% of the number of the asymmetric centers (*) having $R^1$ groups with one or more phosphonic acid ester function(s) or phosphonic acid function(s) exhibit the R configuration or the S configuration, and at most 50% of the number of the $R^1$ groups being substituted with phosphonic acid ester functions or phosphonic acid functions.

4. Compound according to claim 1, wherein all asymmetric centers (*) have the same configuration.

5. Compound according to claim 1, wherein all asymmetric centers (*) have a (S) configuration.

6. Compound according to claim 1, wherein all asymmetric centers (*) have a (R)-configuration.

7. Composition which contains at least one compound according to claim 1.

8. Pharmaceutical composition, which contains at least one compound according to claim 1, and, optionally, at least one carrier, solvent or other pharmaceutical adjuvant.

9. Compound according to claim 1, wherein each of the groups represented by K and L is not substituted.

10. Compound according to claim 3, wherein each of the groups represented by K and L is not substituted.

11. Compound according to claim 1, wherein each $R^1$ independently of each other represents a hydrogen atom or an optionally substituted alkyl or alkenyl group having up to 10 carbon atoms.

12. Compound according to claim 3, wherein each $R^1$ independently of each other represents a hydrogen atom or an optionally substituted alkyl or alkenyl group having up to 10 carbon atoms.

13. Compound according to claim 9, wherein each $R^1$ independently of each other represents a hydrogen atom or an optionally substituted alkyl or alkenyl group having up to 10 carbon atoms.

14. Compound according to claim 10, wherein each $R^1$ independently of each other represents a hydrogen atom or an optionally substituted alkyl or alkenyl group having up to 10 carbon atoms.

* * * * *